(12) United States Patent
Radmer et al.

(10) Patent No.: US 7,955,297 B2
(45) Date of Patent: Jun. 7, 2011

(54) RETRACTION MEANS FOR TRANSCUTANEOUS DEVICE

(75) Inventors: Jim Radmer, Fredensborg (DK); Erik Winkel Ethelfeld, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 353 days.

(21) Appl. No.: 10/566,795

(22) PCT Filed: Jul. 30, 2004

(86) PCT No.: PCT/DK2004/000516
§ 371 (c)(1),
(2), (4) Date: Aug. 30, 2006

(87) PCT Pub. No.: WO2005/011779
PCT Pub. Date: Feb. 10, 2005

(65) Prior Publication Data
US 2007/0049865 A1 Mar. 1, 2007

Related U.S. Application Data

(60) Provisional application No. 60/496,112, filed on Aug. 19, 2003.

(30) Foreign Application Priority Data

Aug. 1, 2003 (EP) .................................... 03388053

(51) Int. Cl.
*A61M 31/00* (2006.01)
(52) U.S. Cl. ........... 604/93.01; 604/164.01; 604/164.04; 604/264; 604/272; 604/110
(58) Field of Classification Search .................... 604/19, 604/21, 158, 164.01, 164.04, 164.12, 165.03, 604/166.01, 170.02, 264, 272, 110, 223, 604/224, 93.01, 180
See application file for complete search history.

(56) References Cited

U.S. PATENT DOCUMENTS
2,605,765 A 8/1952 Kollsman
(Continued)

FOREIGN PATENT DOCUMENTS
CA 2239457 12/1999
(Continued)

OTHER PUBLICATIONS

International Search Report mailed Jul. 5, 2007 in international application No. PCT/EP2007/053923.
(Continued)

*Primary Examiner* — Nicholas D Lucchesi
*Assistant Examiner* — Quynh-Nhu H Vu
(74) *Attorney, Agent, or Firm* — Marc A. Began

(57) ABSTRACT

The invention provides a transcutaneous medical device (502, 250, 150, 600) comprising a lower surface adapted for application towards the skin of a subject, attaching means (571, 272, 161) for securing the lower surface relative to the skin, and a transcutaneous device (530, 182, 213, 651) adapted to penetrate the skin of the subject. The transcutaneous device is mounted for movement between an extended position in which the transcutaneous device projects relative to the lower surface and a retracted position in which the transcutaneous device is retracted relative to the lower surface. The medical device further comprises release means (550, 275, 162) which can be operated from a first state through an intermediate state to a second state, whereby operation of the release means from the first to the intermediate state causes the transcutaneous device to be moved from the extended position to the retracted position, and operation of the release means from the intermediate to the second state causes release of the attaching means.

24 Claims, 19 Drawing Sheets

U.S. PATENT DOCUMENTS

| | | |
|---|---|---|
| 2,960,097 A | 11/1960 | Scheffler |
| 2,980,032 A | 4/1961 | Schneider |
| 3,705,601 A | 12/1972 | Arisland |
| 4,016,879 A | 4/1977 | Mellor |
| 4,077,405 A | 3/1978 | Haerten et al. |
| 4,137,020 A | 1/1979 | Ito et al. |
| 4,245,634 A | 1/1981 | Albisser et al. |
| 4,262,824 A | 4/1981 | Hrynewycz |
| 4,340,048 A | 7/1982 | Eckenhoff |
| 4,370,305 A | 1/1983 | Affonso |
| 4,378,015 A | 3/1983 | Wardlaw |
| 4,399,824 A | 8/1983 | Davidson |
| 4,402,407 A | 9/1983 | Maly |
| 4,519,792 A | 5/1985 | Dawe |
| 4,529,401 A | 7/1985 | Leslie et al. |
| 4,544,369 A | 10/1985 | Skakoon et al. |
| 4,552,561 A | 11/1985 | Eckenhoff et al. |
| 4,645,491 A | 2/1987 | Evans |
| 4,657,490 A | 4/1987 | Abbott |
| 4,710,170 A | 12/1987 | Haber et al. |
| 4,734,092 A | 3/1988 | Millerd |
| 4,753,651 A | 6/1988 | Eckenhoff |
| 4,755,173 A | 7/1988 | Konopka et al. |
| 4,788,556 A | 11/1988 | Hoisington et al. |
| 4,871,351 A | 10/1989 | Feingold |
| 4,877,034 A | 10/1989 | Atkins et al. |
| 4,886,499 A | 12/1989 | Cirelli et al. |
| 4,894,054 A | 1/1990 | Miskinyar |
| 4,928,528 A | 5/1990 | Marques |
| 4,994,078 A | 2/1991 | Jarvik |
| 5,008,110 A | 4/1991 | Benecke et al. |
| 5,049,146 A | 9/1991 | Bringham et al. |
| 5,076,890 A | 12/1991 | Balembois |
| 5,122,116 A | 6/1992 | Kriesel et al. |
| 5,122,201 A | 6/1992 | Frazier et al. |
| 5,149,340 A | 9/1992 | Waycuilis |
| 5,169,390 A | 12/1992 | Athayde et al. |
| 5,211,201 A | 5/1993 | Kamen et al. |
| 5,224,843 A | 7/1993 | van Lintel |
| 5,256,157 A | 10/1993 | Samiotes et al. |
| 5,336,052 A | 8/1994 | Zöllner et al. |
| 5,390,671 A | 2/1995 | Lord et al. |
| 5,391,950 A | 2/1995 | Krawczak |
| 5,482,473 A | 1/1996 | Lord et al. |
| 5,485,917 A | 1/1996 | Early |
| 5,494,415 A | 2/1996 | Morita |
| 5,514,095 A | 5/1996 | Brightbill et al. |
| 5,527,287 A | 6/1996 | Miskinyar |
| 5,527,288 A | 6/1996 | Gross et al. |
| 5,568,806 A | 10/1996 | Cheney, II et al. |
| 5,584,808 A | 12/1996 | Healy |
| 5,584,813 A | 12/1996 | Livingston et al. |
| 5,586,085 A | 12/1996 | Lichte |
| 5,609,572 A | 3/1997 | Lang |
| 5,647,853 A | 7/1997 | Feldmann et al. |
| 5,720,391 A | 2/1998 | Dohm et al. |
| 5,776,109 A | 7/1998 | Urrutia |
| 5,814,020 A | 9/1998 | Gross |
| 5,851,197 A | 12/1998 | Marano et al. |
| 5,858,001 A | 1/1999 | Tsals et al. |
| 5,860,952 A | 1/1999 | Quinn |
| 5,913,856 A | 6/1999 | Chia et al. |
| 5,925,017 A | 7/1999 | Kriesel et al. |
| 5,928,194 A | 7/1999 | Maget |
| 5,931,814 A | 8/1999 | Alex et al. |
| 5,941,611 A | 8/1999 | Trzmiel et al. |
| 5,954,643 A | 9/1999 | VanAntwerp et al. |
| 5,957,895 A | 9/1999 | Sage et al. |
| 5,968,011 A | 10/1999 | Larsen et al. |
| 5,997,501 A | 12/1999 | Gross et al. |
| 6,045,534 A | 4/2000 | Jacobsen et al. |
| 6,060,319 A | 5/2000 | Deetz et al. |
| 6,074,369 A | 6/2000 | Sage et al. |
| 6,083,196 A | 7/2000 | Trautman et al. |
| 6,088,619 A | 7/2000 | Hein et al. |
| 6,099,512 A | 8/2000 | Urrutia |
| 6,120,492 A | 9/2000 | Finch et al. |
| 6,123,519 A | 9/2000 | Kato et al. |
| 6,126,637 A | 10/2000 | Kriesel et al. |
| 6,132,755 A | 10/2000 | Eicher et al. |
| 6,165,155 A | 12/2000 | Jacobsen et al. |
| 6,241,704 B1 | 6/2001 | Peterson et al. |
| 6,270,478 B1 | 8/2001 | Mernøe |
| 6,280,148 B1 | 8/2001 | Zengerle et al. |
| 6,293,925 B1 | 9/2001 | Safabash et al. |
| 6,302,866 B1 | 10/2001 | Marggi |
| 6,302,869 B1 | 10/2001 | Klitgaard |
| 6,358,731 B1 | 3/2002 | Hsu |
| 6,364,865 B1 | 4/2002 | Lavi et al. |
| 6,485,461 B1 | 11/2002 | Mason et al. |
| 6,500,150 B1 | 12/2002 | Gross et al. |
| 6,551,276 B1 | 4/2003 | Mann et al. |
| 6,554,791 B1 | 4/2003 | Cartledge et al. |
| 6,555,986 B2 | 4/2003 | Moberg |
| 6,558,351 B1 | 5/2003 | Steil et al. |
| 6,589,229 B1 | 7/2003 | Connelly et al. |
| 6,613,015 B2 * | 9/2003 | Sandstrom et al. ............ 604/110 |
| 6,622,037 B2 | 9/2003 | Kasano |
| 6,656,159 B2 | 12/2003 | Flaherty |
| 6,716,192 B1 | 4/2004 | Orosz |
| 6,740,059 B2 | 5/2004 | Flaherty |
| 6,749,587 B2 | 6/2004 | Flaherty |
| 6,808,691 B1 | 10/2004 | Herve et al. |
| 6,818,178 B2 | 11/2004 | Kohl et al. |
| 6,878,136 B2 | 4/2005 | Fleury et al. |
| 6,949,084 B2 | 9/2005 | Marggi et al. |
| 6,960,192 B1 | 11/2005 | Flaherty et al. |
| 7,052,483 B2 | 5/2006 | Wojcik |
| 7,070,580 B2 | 7/2006 | Nielsen |
| 7,097,631 B2 | 8/2006 | Trautman et al. |
| 7,097,690 B2 | 8/2006 | Usher et al. |
| 7,141,023 B2 | 11/2006 | Diermann et al. |
| 7,144,384 B2 | 12/2006 | Gorman et al. |
| 7,303,073 B2 | 12/2007 | Raynal-Olive et al. |
| 7,744,570 B2 | 6/2010 | Fangrow |
| 2001/0025168 A1 * | 9/2001 | Gross et al. .................. 604/506 |
| 2002/0040083 A1 | 4/2002 | Kuwaki et al. |
| 2002/0040208 A1 | 4/2002 | Flaherty et al. |
| 2002/0055711 A1 * | 5/2002 | Lavi et al. ..................... 604/110 |
| 2002/0064468 A1 | 5/2002 | Wade |
| 2002/0123740 A1 | 9/2002 | Flaherty et al. |
| 2002/0161332 A1 | 10/2002 | Ramey |
| 2002/0169416 A1 | 11/2002 | Gonnelli et al. |
| 2003/0009131 A1 | 1/2003 | Van Antwerp et al. |
| 2003/0009133 A1 | 1/2003 | Ramey |
| 2003/0029501 A1 | 2/2003 | Williamson et al. |
| 2003/0060781 A1 | 3/2003 | Mogensen et al. |
| 2003/0065308 A1 | 4/2003 | Lebel et al. |
| 2003/0069546 A1 | 4/2003 | Sandstrom et al. |
| 2003/0073952 A1 | 4/2003 | Flaherty et al. |
| 2003/0088238 A1 | 5/2003 | Poulsen et al. |
| 2003/0114797 A1 | 6/2003 | Vaillancourt et al. |
| 2003/0135159 A1 | 7/2003 | Daily et al. |
| 2003/0167035 A1 | 9/2003 | Flaherty et al. |
| 2003/0187395 A1 | 10/2003 | Gabel et al. |
| 2003/0194328 A1 | 10/2003 | Bryant et al. |
| 2003/0199823 A1 | 10/2003 | Bobroff et al. |
| 2003/0216686 A1 | 11/2003 | Lynch et al. |
| 2003/0236498 A1 | 12/2003 | Gross et al. |
| 2004/0051674 A1 | 3/2004 | Mahringer |
| 2004/0087240 A1 | 5/2004 | Chen et al. |
| 2004/0098068 A1 | 5/2004 | Carbunaru et al. |
| 2004/0115068 A1 | 6/2004 | Hansen et al. |
| 2004/0116905 A1 | 6/2004 | Pedersen et al. |
| 2004/0127844 A1 | 7/2004 | Flaherty |
| 2004/0158207 A1 | 8/2004 | Hunn et al. |
| 2004/0162521 A1 | 8/2004 | Bengtsson |
| 2004/0171403 A1 | 9/2004 | Mikkola |
| 2004/0199123 A1 | 10/2004 | Nielsen |
| 2004/0204673 A1 | 10/2004 | Flaherty et al. |
| 2004/0220497 A1 | 11/2004 | Findlay et al. |
| 2004/0220536 A1 | 11/2004 | VanTassel et al. |
| 2004/0260233 A1 | 12/2004 | Garibotto et al. |
| 2005/0006309 A1 | 1/2005 | Effenhauser et al. |
| 2005/0022274 A1 | 1/2005 | Campbell et al. |
| 2005/0077225 A1 | 4/2005 | Usher et al. |
| 2005/0101933 A1 | 5/2005 | Marrs et al. |

| | | | |
|---|---|---|---|
| 2005/0171513 A1 | 8/2005 | Mann et al. | |
| 2005/0203461 A1 | 9/2005 | Flaherty et al. | |
| 2005/0240154 A1 | 10/2005 | Mogensen et al. | |
| 2006/0015063 A1 | 1/2006 | Butikofer et al. | |
| 2006/0017576 A1 | 1/2006 | Gordon et al. | |
| 2006/0020300 A1 | 1/2006 | Nghiem et al. | |
| 2006/0142698 A1 | 6/2006 | Ethelfeld | |
| 2006/0200073 A1* | 9/2006 | Radmer et al. | 604/93.01 |
| 2006/0264835 A1* | 11/2006 | Nielsen et al. | 604/174 |
| 2007/0021733 A1* | 1/2007 | Hansen et al. | 604/890.1 |
| 2007/0073228 A1 | 3/2007 | Mernoe et al. | |
| 2007/0104596 A1 | 5/2007 | Preuthun et al. | |
| 2007/0112301 A1 | 5/2007 | Preuthun et al. | |
| 2008/0009805 A1 | 1/2008 | Ethelfeld | |
| 2009/0163874 A1 | 6/2009 | Krag et al. | |

FOREIGN PATENT DOCUMENTS

| | | |
|---|---|---|
| CN | 1612758 | 5/2005 |
| DE | 2552446 | 11/1975 |
| DE | 10255817 | 6/2004 |
| DK | PA 2003 00696 | 5/2003 |
| DK | PA 2003 00697 | 5/2003 |
| EP | 398583 | 11/1990 |
| EP | 568176 | 11/1993 |
| EP | 937475 | 8/1999 |
| EP | 1177802 | 7/2001 |
| EP | 1329233 | 12/2001 |
| EP | 1256356 | 5/2002 |
| EP | 1475113 | 5/2003 |
| EP | 1527792 | 5/2005 |
| GB | 2020735 | 11/1979 |
| GB | 2212387 | 7/1989 |
| JP | 2000-104659 | 4/2000 |
| JP | 2000-513259 | 10/2000 |
| JP | 2000-515394 | 11/2000 |
| JP | 2002-505601 | 2/2002 |
| WO | WO 90/07942 | 7/1990 |
| WO | WO 96/07397 | 3/1996 |
| WO | WO 96/30679 | 10/1996 |
| WO | WO 97/21457 | 6/1997 |
| WO | 9857683 | 6/1998 |
| WO | 9962576 | 12/1999 |
| WO | 0202165 | 1/2002 |
| WO | WO 02/04048 | 1/2002 |
| WO | WO 02/05889 | 1/2002 |
| WO | 0215965 | 2/2002 |
| WO | WO 02/15889 | 2/2002 |
| WO | WO 02/40083 | 5/2002 |
| WO | 0245574 | 6/2002 |
| WO | WO 02/47746 | 6/2002 |
| WO | WO 02/055132 | 7/2002 |
| WO | WO 02/070024 | 9/2002 |
| WO | WO 02/081012 | 10/2002 |
| WO | WO 02/100457 | 12/2002 |
| WO | WO 03/026726 | 4/2003 |
| WO | WO 03/026728 | 4/2003 |
| WO | 03099358 | 5/2003 |
| WO | WO 03/080169 | 10/2003 |
| WO | WO 03/089028 | 10/2003 |
| WO | WO 03/090509 | 11/2003 |
| WO | WO 2004/009160 | 1/2004 |
| WO | WO 2004/029457 | 4/2004 |
| WO | WO 2004/030728 | 4/2004 |
| WO | WO 2004/098682 | 11/2004 |
| WO | WO 2004/098683 | 11/2004 |
| WO | WO 2004/098684 | 11/2004 |
| WO | WO 2004/101071 | 11/2004 |
| WO | WO 2005/002649 | 1/2005 |
| WO | WO 2005/011779 | 2/2005 |
| WO | WO 2005/025652 | 3/2005 |
| WO | WO 2005/037185 | 4/2005 |
| WO | WO 2005/037350 | 4/2005 |
| WO | WO 2005/039673 | 5/2005 |
| WO | WO 2005/094919 | 10/2005 |
| WO | WO 2005/123186 | 12/2005 |
| WO | WO 2005/123189 | 12/2005 |
| WO | WO 2006/060277 | 6/2006 |
| WO | WO 2006/067217 | 6/2006 |
| WO | WO 2006/077263 | 7/2006 |
| WO | WO 2006/089958 | 8/2006 |
| WO | WO 2006/120253 | 11/2006 |
| WO | WO 2006/123329 | 11/2006 |
| WO | WO 2007/122207 | 11/2007 |
| WO | WO 2009/021950 | 2/2009 |

OTHER PUBLICATIONS

International Preliminary Examination Report issued in connection with counterpart PCT Application No. PCT/EP2006/062301, mailed Nov. 22, 2007.
International Search Report and Written Opinion issued in connection with counterpart international application No. PCT/EP2006/062301, mailed Nov. 2, 2006.
International Search Report mailed May 24, 2006 in international application No. PCT/EP2006/050410.
Office Action Issued in Connection With Counterpart Danish Application No. PA 2005 00703, Mailed Mar. 3, 2006.
CN 1612758 English Abstract, published Feb. 6, 2008.
DE 10255817 English Abstract, published Jun. 17, 2004.
DE 2552446 English Abstract, published May 26, 1977, DE 2552446.
JP 2002-505601 Machine Translation, published Feb. 19, 2002.
JP 2000-515394 Machine Translation, published Nov. 21, 2000.
JP 2000-513259 Machine Translation, published Oct. 10, 2000.
JP 2000-104659 Machine Translation, published Apr. 11, 2000.
Final Office Action mailed Apr. 16, 2010 in U.S. Appl. No. 12/303,307, filed Feb. 20, 2009 by Krag.
Non-Final Office Action mailed Nov. 27, 2009 in U.S. Appl. No. 12/303,307, filed Feb. 20, 2009 by Krag.
Non-Final Office Action mailed Apr. 6, 2010 in U.S. Appl. No. 12/298,253, filed Dec. 8, 2008 by Krag et al.
Final Office Action mailed Apr. 28, 2010 in U.S. Appl. No. 12/066,712, filed Mar. 13, 2008 by Hansen et al.
Non-Final Office Action mailed Oct. 27, 2009 in U.S. Appl. No. 12/066,712, filed Mar. 13, 2008 by Hansen et al.
Non-Final Office Action mailed Apr. 10, 2009 in U.S. Appl. No. 12/066,712, filed Mar. 13, 2008 by Hansen et al.
Final Office Action mailed Jul. 16, 2010 in U.S. Appl. No. 11/913,689, filed Dec. 12, 2007 by Hansen et al.
Non-Final Office Action mailed Mar. 15, 2010 in U.S. Appl. No. 11/913,689, filed Dec. 12, 2007 by Hansen et al.
Final Office Action mailed Nov. 25, 2009 in U.S. Appl. No. 11/913,689, filed Dec. 12, 2007 by Hansen et al.
Non-Final Office Action mailed May 8, 2009 in U.S. Appl. No. 11/913,689, filed Dec. 12, 2007 by Hansen et al.
Non-Final Office Action mailed Apr. 30, 2010 in U.S. Appl. No. 11/911,213, filed Oct. 11, 2007 by Nielsen et al.
Non-Final Office Action mailed Jul. 24, 2009 in U.S. Appl. No. 11/911,213, filed Oct. 11, 2007 by Nielsen et al.
Final Office Action mailed Nov. 17, 2009 in U.S. Appl. No. 11/816,729, filed Nov. 15, 2007 by Larsen et al.
Non-Final Office Action mailed Apr. 17, 2009 in U.S. Appl. No. 11/816,729, filed Nov. 15, 2007 by Larsen et al.
Non-Final Office Action mailed Jul. 23, 2010 in U.S. Appl. No. 11/813,433, filed Apr. 30, 2008 by Teisen-Simony et al.
Non-Final Office Action mailed Apr. 28, 2010 in U.S. Appl. No. 11/813,381, filed Apr. 11, 2008 by Teisen-Simony et al.
Final Office Action mailed Nov. 3, 2009 in U.S. Appl. No. 11/792,355, filed Apr. 23, 2008 by Ethelfeld et al.
Non-Final Office Action mailed Feb. 17, 2009 in U.S. Appl. No. 11/792,355, filed Apr. 23, 2008 by Ethelfeld et al.
Final Office Action mailed Dec. 29, 2009 in U.S. Appl. No. 11/663,048, filed Nov. 15, 2007 by Thorkild et al.
Non-Final Office Action mailed Apr. 17, 2009 in U.S. Appl. No. 11/663,048, filed Nov. 15, 2007 by Thorkild et al.
Notice of Abandonment mailed Oct. 23, 2007 in U.S. Appl. No. 11/662,905, filed Sep. 22, 2005 by Ahm et al.
Non-Final Office Action mailed May 19, 2010 in U.S. Appl. No. 11/541,348, filed Sep. 29, 2006 by Preuthun et al.
Final Office Action mailed Jan. 8, 2010 in U.S. Appl. No. 11/541,348, filed Sep. 29, 2006 by Preuthun et al.

Non-Final Office Action mailed May 22, 2009 in U.S. Appl. No. 11/541,348, filed Sep. 29, 2006 by Preuthun et al.
Response and Amendment filed Jan. 29, 2009 in U.S. Appl. No. 11/541,348, filed Sep. 29, 2006 by Preuthun et al.
Final Office Action mailed Oct. 29, 2008 in U.S. Appl. No. 11/541,348, filed Sep. 29, 2006 by Preuthun et al.
Response and Amendment filed Jul. 16, 2008 in U.S. Appl. No. 11/541,348, filed Sep. 29, 2006 by Preuthun et al.
Non-Final Office Action mailed Apr. 18, 2008 in U.S. Appl. No. 11/541,348, filed Sep. 29, 2006 by Preuthun et al.
Final Office Action mailed May 5, 2010 in U.S. Appl. No. 11/540,842, filed Sep. 29, 2006 by Preuthun et al.
Non-Final Office Action mailed Sep. 28, 2009 in U.S. Appl. No. 11/540,842, filed Sep. 29, 2006 by Preuthun et al.
Response and Amendment filed Aug. 7, 2009 in U.S. Appl. No. 11/540,842, filed Sep. 29, 2006 by Preuthun et al.
Final Office Action mailed May 13, 2009 in U.S. Appl. No. 11/540,842, filed Sep. 29, 2006 by Preuthun et al.
Response and Amendment filed Mar. 11, 2009 in U.S. Appl. No. 11/540,842, filed Sep. 29, 2006 by Preuthun et al.
Non-Final Office Action mailed Dec. 12, 2008 in U.S. Appl. No. 11/540,842, filed Sep. 29, 2006 by Preuthun et al.
Response and Amendment filed Oct. 10, 2008 in U.S. Appl. No. 11/540,842, filed Sep. 29, 2006 by Preuthun et al.
Final Office Action mailed Jul. 11, 2008 in U.S. Appl. No. 11/540,842, filed Sep. 29, 2006 by Preuthun et al.
Response and Amendment filed May 20, 2008 in U.S. Appl. No. 11/540,842, filed Sep. 29, 2006 by Preuthun et al.
Non-Final Office Action mailed Feb. 25, 2008 in U.S. Appl. No. 11/540,842, filed Sep. 29, 2006 by Preuthun et al.
Final Office Action mailed Aug. 5, 2009 in U.S. Appl. No. 11/407,647, filed Apr. 20, 2006 by Hansen et al.
Non-Final Office Action mailed Feb. 6, 2009 in U.S. Appl. No. 11/407,647, filed Apr. 20, 2006 by Hansen et al.
Final Office Action mailed Sep. 29, 2008 in U.S. Appl. No. 11/407,647, filed Apr. 20, 2006 by Hansen et al.
Non-Final Office Action mailed Feb. 28, 2008 in U.S. Appl. No. 11/407,647, filed Apr. 20, 2006 by Hansen et al.
Non-Final Office Action mailed Aug. 19, 2010 in U.S. Appl. No. 11/266,905, filed Nov. 4, 2005 by Ethelfeld et al.
Final Office Action mailed Oct. 30, 2009 in U.S. Appl. No. 11/266,905, filed Nov. 4, 2005 by Ethelfeld et al.
Non-Final Office Action mailed Mar. 18, 2009 in U.S. Appl. No. 11/266,905, filed Nov. 4, 2005 by Ethelfeld et al.
Non-Final Office Action mailed Aug. 25, 2008 in U.S. Appl. No. 11/266,905, filed Nov. 4, 2005 by Ethelfeld et al.
Final Office Action mailed Oct. 5, 2007 in U.S. Appl. No. 11/266,905, filed Nov. 4, 2005 by Ethelfeld et al.
Non-Final Office Action mailed Mar. 27, 2007 in U.S. Appl. No. 11/266,905, filed Nov. 4, 2005 by Ethelfeld et al.
Notice of Abandonment mailed Oct. 12, 2010 in U.S. Appl. No. 11/266,904, filed Nov. 4, 2005 by Ethelfeld et al.
Second Advisory Action mailed Aug. 13, 2008 in U.S. Appl. No. 11/266,904, filed Nov. 4, 2005 by Ethelfeld et al.
First Advisory Action mailed Dec. 28, 2007 in U.S. Appl. No. 11/266,904, filed Nov. 4, 2005 by Ethelfeld et al.
Final Office Action mailed Sep. 11, 2007 in U.S. Appl. No. 11/266,904, filed Nov. 4, 2005 by Ethelfeld et al.
Non-Final Office Action mailed Jan. 5, 2007 in U.S. Appl. No. 11/266,904, filed Nov. 4, 2005 by Ethelfeld et al.
Requirement for Restriction mailed May 22, 2006 in U.S. Appl. No. 11/266,904, filed Nov. 4, 2005 by Ethelfeld et al.
Notice of Allowance mailed Jul. 15, 2009 in U.S. Appl. No. 11/266,821, filed Nov. 4, 2005 by Ethelfeld et al.
Non-Final Office Action mailed Jan. 29, 2009 in U.S. Appl. No. 11/266,821, filed Nov. 4, 2005 by Ethelfeld et al.
Final Office Action mailed Jul. 18, 2008 in U.S. Appl. No. 11/266,821, filed Nov. 4, 2005 by Ethelfeld et al.
Non-Final Office Action mailed Mar. 28, 2008 in U.S. Appl. No. 11/266,821, filed Nov. 4, 2005 by Ethelfeld et al.
Final Office Action mailed Oct. 16, 2009 in U.S. Appl. No. 11/250,233, filed Oct. 14, 2005 by Ethelfeld et al.
Non-Final Office Action mailed Mar. 12, 2009 in U.S. Appl. No. 11/250,233, filed Oct. 14, 2005 by Ethelfeld et al.
US 6,197,009, 03/2001, Steg (withdrawn)

* cited by examiner

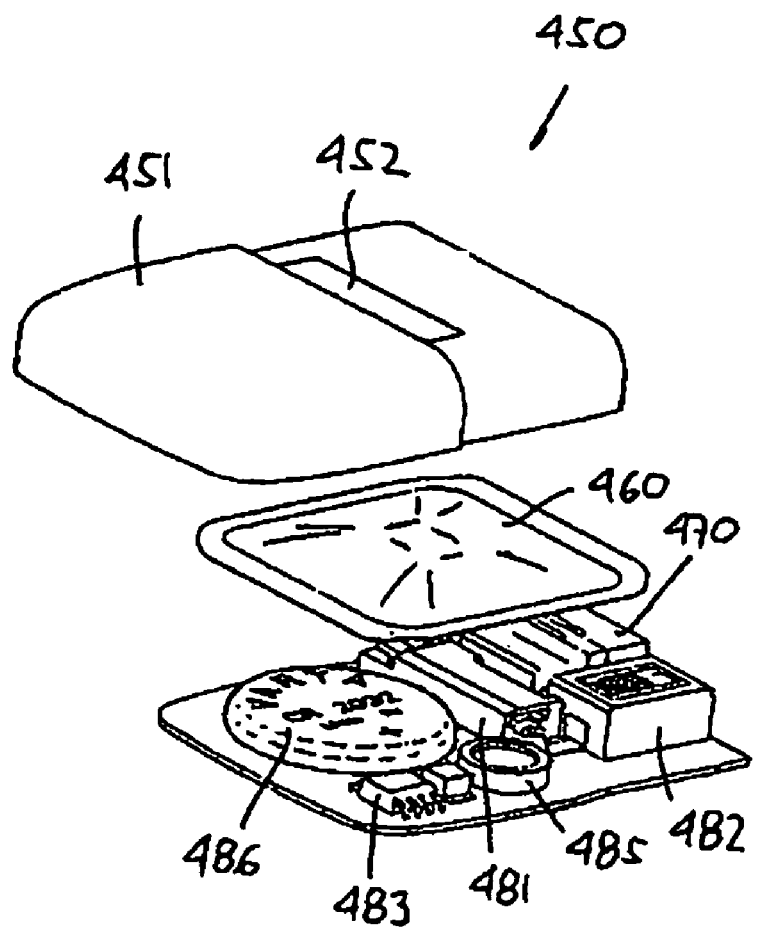

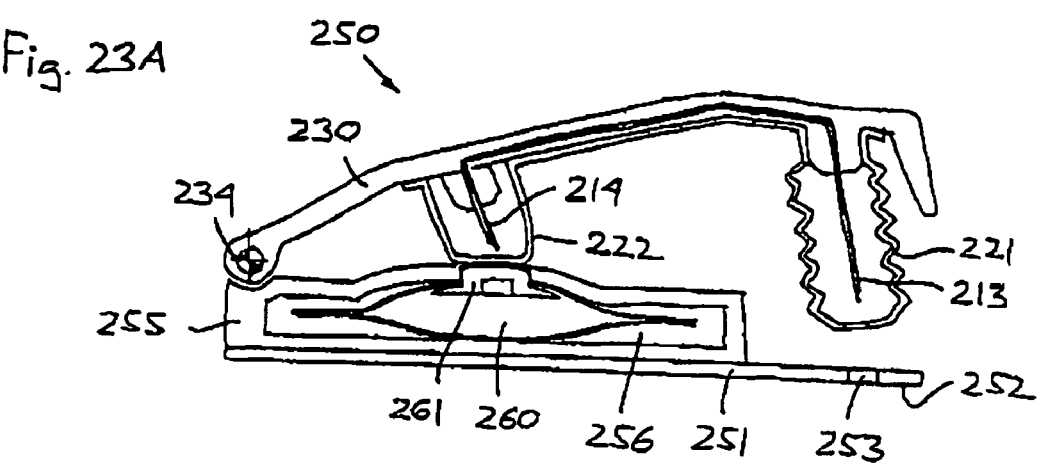
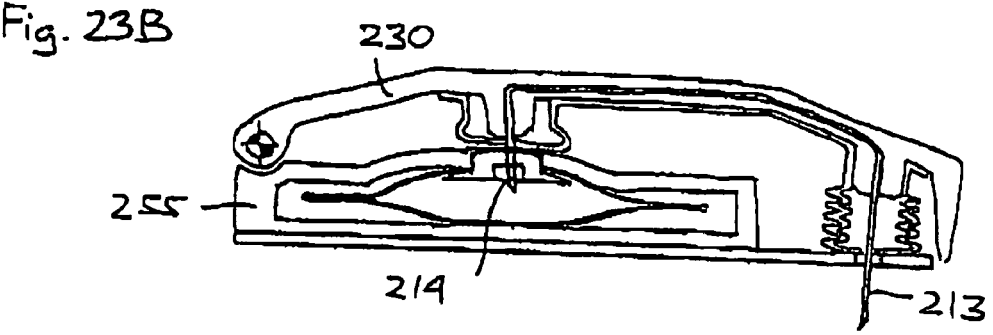

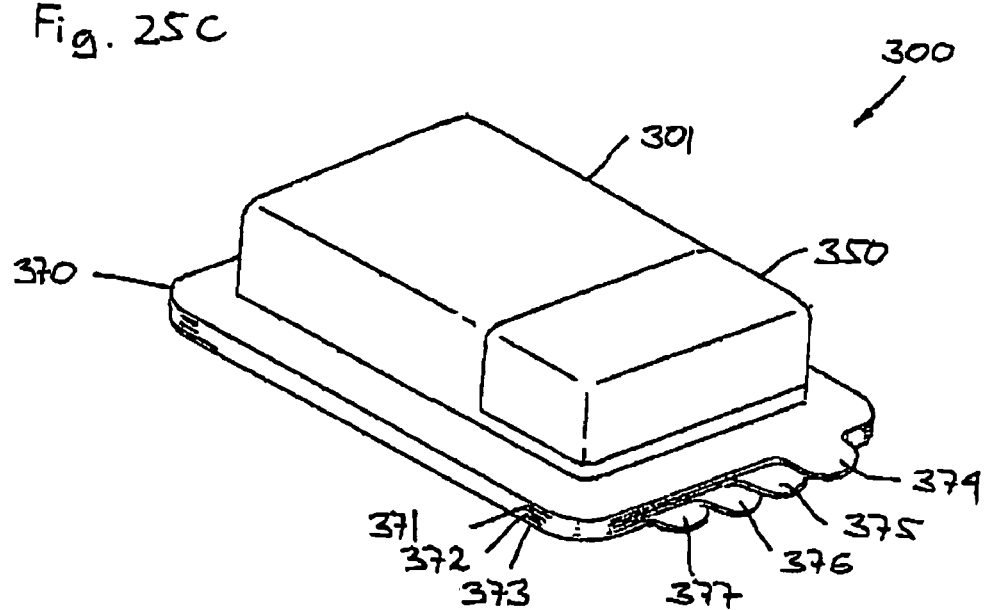
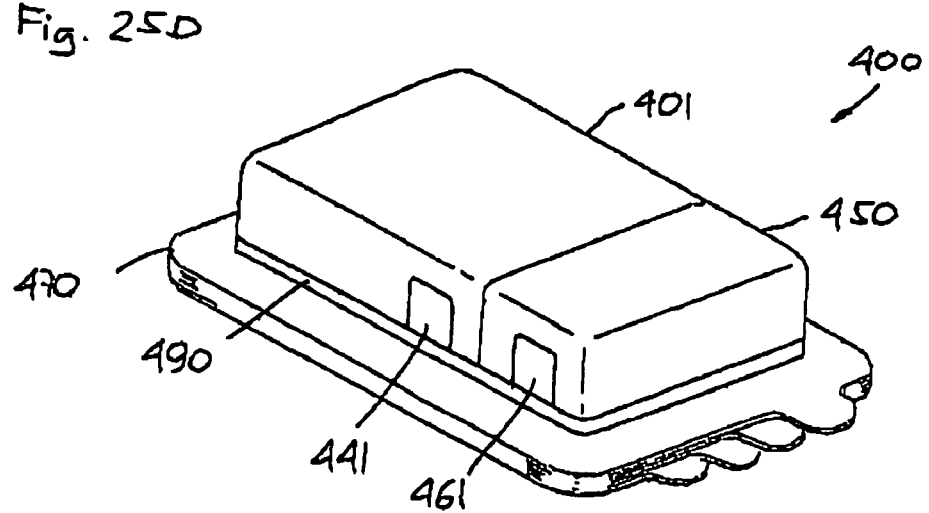

RETRACTION MEANS FOR TRANSCUTANEOUS DEVICE

CROSS-REFERENCE TO RELATED APPLICATIONS

This application is a 35 U.S.C. §371 national stage application of International Patent Application PCT/DK2004/00516 (published as WO 2005/011779), filed Jul. 30, 2004, which claims priority of European Patent Application 03388053.5, filed Aug. 1, 2003 and to U.S. Patent Application No. 60/496,112, filed Aug. 19, 2003 under 35 U.S.C. §119.

The present invention generally relates to retraction of transcutaneous devices such as needles, needle-like members and cannulas adapted for insertion at a selected site within the body of a subject for subcutaneous, intravenous, intramuscular or intradermal placement, the transcutaneous device being carried by a device comprising a lower surface adapted for application towards the skin of a subject. The invention also relates to release means for releasing a medical device from a given site, the medical device comprising a transcutaneous device.

BACKGROUND OF THE INVENTION

In the disclosure of the present invention reference is mostly made to the treatment of diabetes by injection or infusion of insulin, however, this is only an exemplary use of the present invention.

Portable drug delivery devices for delivering a drug to a patient are well known and generally comprise a reservoir adapted to contain a liquid drug and having an outlet in fluid communication with a hollow infusion needle, as well as expelling means for expelling a drug out of the reservoir and through the skin of the subject via the hollow needle. Such devices are often termed infusion pumps.

Basically, infusion pumps can be divided into two classes. The first class comprises relatively expensive infusion pumps intended for 3-4 years use, for which reason the initial cost for such a pump often is a barrier to this type of therapy. Although more complex than traditional syringes and pens, the pump offer the advantages of continuous infusion of insulin, precision in dosing and optionally programmable delivery profiles and user actuated bolus infusions in connections with meals.

Addressing the above problem, several attempts have been made to provide a second class of drug infusion devices that are low in cost and convenient to use. Some of these devices are intended to be partially or entirely disposable and may provide many of the advantages associated with an infusion pump without the attendant cost and inconveniences, e.g. the pump may be prefilled thus avoiding the need for filling or refilling a drug reservoir. Examples of this type of infusion devices are known from U.S. Pat. Nos. 4,340,048 and 4,552,561 (based on osmotic pumps), U.S. Pat. No. 5,858,001 (based on a piston pump), U.S. Pat. No. 6,280,148 (based on a membrane pump), U.S. Pat. No. 5,957,895 (based on a flow restrictor pump (also know as a bleeding hole pump), U.S. Pat. No. 5,527,288 (based on a gas generating pump), or U.S. Pat. No. 5,814,020 (based on a swellable gel) which all in the last decades have been proposed for use in inexpensive, primarily disposable drug infusion devices, the cited documents being incorporated by reference.

The disposable pumps generally comprises a skin-contacting mounting surface adapted for application to the skin of a subject by adhesive means, and with the infusion needle arranged such that in a situation of use it projects from the mounting surface to thereby penetrate the skin of the subject, whereby the place where the needle penetrates the skin is covered while the appliance is in use.

The infusion needle may be arranged to permanently project from the mounting surface such that the needle is inserted simultaneously with the application of the infusion pump. Examples of this configuration can be found in U.S. Pat. Nos. 2,605,765, 4,340,048 and in EP 1 177 802. Although this configuration provides a simple and cost-effective solution, the actual user-performed piercing of the tissue with the needle is often problematic as people who are not experts in medicine are usually insufficiently practised to place such a needle correctly and they often suffer from a fear of the likely pain. Although not relating specifically to infusion pumps, U.S. Pat. No. 5,851,197 discloses an injector in which an infusion set comprising a skin-mountable surface with a protruding needle can be mounted, the injector upon actuation driving the entire infusion set into contact with a skin portion whereby the needle is inserted through the skin.

Addressing the above problem, infusion pump devices have been proposed in which the pump device is supplied to the user with the needle in a retracted state, i.e. with the distal pointed end of the needle "hidden" inside the pump device, this allowing the user to place the pump device on the skin without the possibility of observing the needle. When first the needle is hidden, at least some of the fear is overcome making the introduction of the needle in a second step less problematic. U.S. Pat. Nos. 5,858,001 and 5,814,020 disclose infusion devices of this type in which an infusion needle is arranged in an upper housing portion pivotably arranged relative to a base plate portion. In this way the user can introduce the needle by pressing the upper portion into engagement with the base plate portion.

To further reduce the fear and pain associated with the introduction of the needle, many recent pump devices have been provided with actuatable needle insertion means, which just has to be released by the user after which e.g. spring means quickly will advance the needle through the skin.

For example, U.S. Pat. No. 5,957,895 discloses a liquid drug delivery device comprising a bent injection needle which is adapted to project through a needle aperture in the bottom surface of the housing in a situation of use. A movable needle carrier is disposed in the housing for carrying the injection needle and for causing the injection end of the needle to project through the needle aperture upon movement of the needle carrier.

U.S. Pat. No. 5,931,814 discloses an infusion device having a housing with a drug reservoir, an infusion needle (or cannula) communicating with the reservoir, means for inserting the needle, and pump means for discharging the reservoir contents through the needle. The needle is fixed relative to the housing and projects beyond the lower skin-contacting surface of the housing to the depth required for injection. The needle is surrounded by a protective element which is moved by spring means from a first end position in which the protective device projects beyond the lower surface of the housing and beyond the needle to a second end position in which the protective device does not project beyond the underside of the casing. An advantage of this design is that the needle is arranged in a fixed position relative to the reservoir. WO 02/15965 discloses a similar infusion device in which a base plate member acts as a protecting element until an upper part of the device, to which the needle is fixed, is moved down into engagement with the base plate member.

In the devices disclosed in U.S. Pat. Nos. 5,957,895 and 5,931,814 the needle is automatically inserted by the release of pre-tensioned spring means arranged within the devices, whereas in the device known from WO 02/15965 the needle is inserted by the user actively moving the hidden needle.

By providing needles which can be inserted after the device has been applied to skin of the user, the risk of needle injuries prior to insertion is reduced, just as the user is not visually confronted with the needle. However, when the device is to be removed from the skin of the user the same problems appear again, i.e. the used needle projecting from the lower surface of the device represents a risk of injury just as the user is visually confronted with the needle. In fact, the risk of serious injuries is considerably higher as the used needle has been exposed to the patient's blood or body fluids, this especially presenting a risk to other persons than the user such as health care personal.

Addressing this problem, WO 02/02165 discloses a needle device having a needle retraction mechanism that retracts the needle upon removing the device from the skin surface. In this device the mechanism "senses" when a portion of the device has been removed from the skin surface. U.S. Pat. No. 5,931,814 discloses a dermally affixed injection device in which a protective element can be moved to cover the needle, the protective element being actuatable before or after the device has been removed from the skin surface of the user.

Before turning to the disclosure of the present invention, a different type of device relying on the insertion of a needle or needle-like structure will be described.

Although drug infusion pumps, either disposable or durable, may provide convenience of use and improved treatment control, it has long been an object to provide a drug infusion system for the treatment of e.g. diabetes which would rely on closed loop control, i.e. being more or less fully automatic, such a system being based on the measurement of a value indicative of the condition treated, e.g. the blood glucose level in case of insulin treatment of diabetes.

A given monitor system for measuring the concentration of a given substance may be based on invasive or non-invasive measuring principles. An example of the latter would be a non-invasive glucose monitor arranged on the skin surface of a patient and using near-IR spectroscopy, however, the present invention is concerned with the introduction of a transcutaneous device such as a needle-formed sensor element.

The sensor may be placed subcutaneously being connected to external equipment by wiring or the substance (e.g. fluid) to be analysed may be transported to an external sensor element, both arrangements requiring the placement of a subcutaneous component (e.g. small catheter or tubing), the present invention addressing both arrangements. However, for simplicity the term "sensor" is used in the following for both types of elements introduced into the subject.

Turning to the sensor elements per se, relatively small and flexible electrochemical sensors have been developed for subcutaneous placement of sensor electrodes in direct contact with patient blood or other extra-cellular fluid (see for example U.S. Pat. No. 5,482,473), wherein such sensors can be used to obtain periodic or continuous readings over a period of time. Insertion devices for this type of sensors are described in, among others, U.S. Pat. Nos. 5,390,671, 5,391,950, 5,568,806 and 5,954,643 which hereby are incorporated by reference.

More specifically, U.S. Pat. No. 5,954,643 discloses an insertion set comprising a mounting base supporting a proximal end of a flexible thin film sensor, the sensor including a distal segment with sensor electrodes thereon which protrudes from the mounting base for transcutaneous placement, wherein the sensor distal segment is slidably carried by a slotted insertion needle fitted through the assembled base. Placement of the insertion set against the patient's skin causes the insertion needle to pierce the skin to carry the sensor electrodes to the desired subcutaneous site, after which the insertion needle can be slidably withdrawn from the insertion set. A similar arrangement is known from U.S. Pat. No. 5,568,806.

DISCLOSURE OF THE INVENTION

Having regard to the above-identified problems, it is an object of the present invention to provide a medical device comprising means for retraction of a transcutaneous device and which is easy to use and provide a high degree of safety against needle injuries. The device should allow for easy and swift, automatic needle retraction, yet being reliable and convenient in use. The device should be compact in size and be designed for cost effective manufacturing.

Correspondingly, a medical device is provided, comprising a lower surface adapted for application towards the skin of a subject, attaching means for securing the lower surface relative to the skin, and a transcutaneous device adapted to penetrate the skin of the subject. The transcutaneous device is mounted for movement between an extended position in which the transcutaneous device projects relative to the lower surface and a retracted position in which the transcutaneous device is retracted relative to the lower surface. The medical device further comprises release means operatable from a first state through an intermediate state to a second state, whereby operation of the release means from the first to the intermediate state causes the transcutaneous device to be moved from the extended position to the retracted position, and operation of the release means from the intermediate to the second state causes release of the attaching means. In this way the transcutaneous device can be retracted before the attaching means is released.

In an embodiment of the invention a medical device is provided comprising a mounting surface adapted for application to a skin site, adhesive means for securing the mounting surface to the skin site, and a transcutaneous device adapted to penetrate the skin at the skin site. The transcutaneous device is mounted for movement between an extended position in which the transcutaneous device projects relative to the lower surface and a retracted position in which the transcutaneous device is retracted relative to the lower surface. The medical device further comprises a release member attached to a peripheral portion of the medical device and comprises a user gripable portion moveable relative to the mounting surface, wherein the release member being moveable to cause the transcutaneous device to be moved from the extended position to the retracted position, the release member further allowing a pulling force to be applied to the peripheral portion of the device to thereby remove the device when secured to the skin site. Although it is defined that adhesive means is provided for securing the mounting surface to the skin site, it readily follows that the adhesive means (e.g. a layer of a medical grade adhesive) constitutes the structure which actually is brought into contact with the skin surface.

By the above arrangement the transcutaneous device can be retracted before the device is removed from the skin. Advantageously, the release member allows the transcutaneous device to be retracted before the user starts to remove the device from the skin surface.

In the context of the present invention the release means responsible for providing the specified functionality may be provided by any suitable structure such as a release, a release member or a release assembly. These structures may be formed by of one or more components, which may be formed integrally, attached to each other or constituting an assembly or structure of functionally interrelated components and members which engage with each other but need not be connected to each other.

The transcutaneous device (which term also covers the similar terms transcutaneous access device and transcutaneous access tool traditionally used in this technical field) may be in the form of a pointed hollow infusion needle, a micro needle array, a pointed needle sensor, or a combination of a relatively flexible per se blunt cannula or sensor device with a pointed insertion needle may provide a pointed transcutaneous device, the insertion needle being retractable after insertion of the blunt portion of the transcutaneous device. In the latter case the portion of the transcutaneous device actually retracted by the retraction means of the present invention does not necessarily comprise a pointed end allowing the combined transcutaneous device to be inserted through the skin, such a pointed end being withdrawn during insertion of the transcutaneous device. The cannula is advantageously soft and flexible relative to the insertion needle which typically is a solid steel needle. In the disclosure of the present invention as well as in the description of the exemplary embodiments, reference will mostly be made to a transcutaneous device in the form of an infusion needle. It should be noted that a micro needle array may be defined as an intradermal device, however, in the present context the term transcutaneous device is used for a device which is adapted for penetrating at least a portion of the skin of a subject for the purpose of introducing a substance into the subject. The length of the transcutaneous device may be chosen in accordance with the actual application, e.g. a hollow steel needle which may be inserted at a substantially right angle relative to the skin surface may have an inserted length of 2-8 mm, preferably 3-5 mm, whereas a cannula which may also be inserted at an oblique angle relative to the skin surface may be somewhat longer, e.g. 4-20 mm.

The lower surface may be a mounting surface adapted for application against the skin of a subject (e.g. user or patient). The mounting surface may be held in contact with the skin by attaching means external to the mounting surface (e.g. coupling means allowing the medical device to be coupled to a skin mountable device, or an adhesive bandage) or by adhesive means provided on the mounting surface. The lower surface may also be adapted for mounting towards the skin via an interposed component of a skin mountable device, e.g. a skin mountable device may comprise a receiving portion to which the medical device is attached, the transcutaneous device being inserted into the skin through an aperture in the receiving portion.

In case adhesive means is provided on the mounting surface, the release means may comprise gripping means connected to a peripheral portion of the mounting surface, whereby operation of the gripping means from a first to an intermediate state causes the needle to be moved from the extended position to the retracted position, and operation of the gripping means from the intermediate to the second state causes the mounting surface to be pulled off the skin of the subject. As appears, whereas retraction of the transcutaneous device may be considered an "action" which may take place in a fraction of a second, the removal (i.e. pulling off) of the adhesive mounting surface from the skin may be characterized as a "process", correspondingly, the period of time when operating the release means from the intermediate to the second state may be somewhat longer than operating the release means from the first to the intermediate state.

In exemplary embodiments the release means comprises transcutaneous device retraction means operable between a first position in which the needle projects relative to the lower surface and a second position in which the transcutaneous device is retracted relative to the lower surface, the retraction means being moved between its first and second positions when the gripping means is operated from the first to the intermediate state. In this way the movement of the transcutaneous device is not necessarily directly linked to the actual movement of gripping means, e.g. the gripping means may be used to release a pre-tensioned retraction mechanism. Further, the transcutaneous device retraction means may be operatable connected to the gripping means by an intermediate member allowing movement of the gripping means to be transferred to the retraction member, e.g. by a pulling string or strip of material. The transcutaneous device retraction means may operate directly on the transcutaneous device or, in case the transcutaneous device is mounted on e.g. a carrier, it may operate indirectly by e.g. engaging the carrier.

In exemplary embodiments the medical device comprises a flexible sheet member having an upper surface connected to a lower surface of a housing or base plate portion of the medical device, the sheet member comprising a lower adhesive surface, the gripping means being connected to the sheet member, advantageously in the form of a tab formed integrally with or attached to the sheet member. The gripping means may also be attached to the housing or base plate portion. To protect the medical device against accidental removal (e.g. during sleep or exercise) the sheet member advantageously extends from the periphery of the housing or base plate portion of the medical device. The sheet member may be of any suitable material, e.g. woven or non-woven medical grade materials normally used for this purpose.

The medical device may be delivered to the user in an initial state with the transcutaneous device extending from the lower surface, such that the transcutaneous device is introduced through the skin as the medical device is mounted relative to the skin surface, however, in exemplary embodiments the transcutaneous device is mounted for movement between an initial position in which the transcutaneous device is retracted relative to the lower surface and the extended position in which the transcutaneous device projects relative to the lower surface. To prevent re-use of the transcutaneous device, the medical device may comprise locking means for locking the transcutaneous device in the retracted position after a single reciprocation of the transcutaneous device from the initial position to the extended position and to the retracted position.

As mentioned above, the medical device of the present invention may comprise transcutaneous devices of different types. For example, the transcutaneous device may comprise a hollow conduit member (e.g. a needle or cannula) for the infusion of a drug, or the transcutaneous device may be in the form of a needle-formed sensor. The medical device may be in the form of an infusion set comprising a fluid conduit adapted for connection to a drug delivery device or adapted for connection to such a fluid conduit.

The medical device may also be in the form of a drug delivery device, further comprising a housing providing the lower surface, a reservoir adapted to contain a liquid drug and comprising an outlet means allowing the transcutaneous device to be arranged in fluid communication with an interior of the reservoir, and expelling means for, in a situation of use, expelling ling a drug out of the reservoir and through the skin of the subject via the transcutaneous device.

The above-described drug delivery device may also be provided as two units, e.g. a transcutaneous device unit (e.g. a needle device or needle unit) as disclosed above, in combination with a pump unit, the pump unit comprising a mounting surface adapted for application against the skin of a subject, a reservoir adapted to contain a liquid drug and comprising an outlet means allowing the transcutaneous device to be arranged in fluid communication with an interior of the reservoir, and expelling means for, in a situation of use, expelling a drug out of the reservoir and through the skin of the subject via a distal end of the transcutaneous device. The attaching means is adapted for securing the transcutaneous device unit to the pump unit and thereby relative to the skin of the subject. In such a combination operation of the release means from the first to the intermediate state causes the transcutaneous device to be moved from the extended position to the retracted position, and operation of the release means from the intermediate to the second state causes release of transcutaneous device unit from the pump unit.

In an exemplary embodiment a transcutaneous device unit comprises a surface adapted for application towards the skin of a subject, a transcutaneous device adapted to penetrate the skin of the subject, the transcutaneous device being mounted for movement between an extended position in which the transcutaneous device projects relative to the surface and a retracted position in which the transcutaneous device is retracted relative to the surface. The transcutaneous device unit further comprises coupling means for releasably securing the unit to a supporting structure, and release means operatable from a first state through an intermediate state to a second state, whereby operation of the release means from the first to the intermediate state causes the transcutaneous device to be moved from the extended position to the retracted position, and operation of the release means from the intermediate to the second state causes release of the coupling means.

In a further embodiment a transcutaneous device unit is provided in combination with a supporting structure, the transcutaneous device unit comprising a surface adapted for application towards the skin of a subject, a transcutaneous device adapted to penetrate the skin of the subject, wherein the transcutaneous device is mounted for movement between an extended position in which the transcutaneous device projects relative to the surface and a retracted position in which the needle is retracted relative to the surface. Further, the needle unit and the supporting structure comprises mating coupling means for releasably securing the transcutaneous device unit to the supporting structure. Release means is arranged on either the needle unit or the supporting structure and being operatable from a first state through an intermediate state to a second state, whereby operation of the release means from the first to the intermediate state causes the transcutaneous device to be moved from the extended position to the retracted position, and operation of the release means from the intermediate to the second state causes release of the coupling means.

The above concept can be regarded as a modular system providing a number of advantages. For example, a given pump unit (either a prefilled pump or a pump adapted to be filled by the user) may be used a number of times with a new transcutaneous device unit. Further, both the pump unit and the transcutaneous device unit may be supplied in a number of variants, e.g. different types of prefilled pumps containing different amounts of different drugs, or different types of e.g. needles or cannulas having different lengths. The transcutaneous device unit may also be in the form of a needle sensor and the "pump unit" may correspondingly be in the form of a device adapted to transmit and/or process data acquired via the sensor.

In exemplary embodiments a receiving portion of the pump unit and a corresponding portion of the needle device comprise releasable coupling means allowing the needle unit to be secured to and released from the pump unit, the coupling means preferably being of mechanical, interlocking nature.

The transcutaneous device may be mounted for movement between an initial position in which the transcutaneous device is retracted relative to the lower surface and the extended position in which the needle projects relative to the lower surface. Advantageously, the transcutaneous device may be moved from its initial to its extended position when the transcutaneous device unit is secured to the pump unit. Also, the transcutaneous device unit may comprise locking means for locking the transcutaneous device in the retracted position after a single reciprocation of the transcutaneous device from the initial position to the extended position and to the retracted position, thereby helping to prevent e.g. accidental needle injuries as well as reuse of the transcutaneous device.

In the above it is described that the medical device of the invention can be used in combination with a drug delivery unit or it can be incorporated in a drug delivery device, such a drug delivery device comprising a reservoir and a drive means, e.g. a pump, for expelling a drug out of the reservoir. This said, such a unit or such a device may comprise one or more detachable subunits, i.e. a durable portion comprising control electronics.

Corresponding to the above described devices, the present invention also provides a method of infusing a medication into a patient, the method comprising the steps of temporarily mounting a medication delivery device on a skin surface of a patient (e.g. by an adhesive provided on the device), extending a transcutaneous device from the medication delivery device thru the skin of a patient, infusing the medication from the medication delivery device into the patient, retracting the transcutaneous device by exerting a force on a release member, and removing the medication delivery device from the patient's skin by continuing to exert a force on the release member. The retracting step and the removing step may be done sequentially without a pause between steps.

The present invention also provides a method of removing a medication delivery device that is adhered to the skin on a patient and comprises a transcutaneous device that is extending thru the skin of a patient, the method comprising the steps of exerting force on a release that is coupled to the transcutaneous device to retract the transcutaneous device from the skin on the patient, and continuing to exert force on the release until the medication delivery device is removed from the skin of the patient.

According to a further aspect of the present invention, a medical device is provided comprising a mounting surface adapted for application to a skin site, an adhesive for securing the mounting surface to the skin site, and a transcutaneous device adapted to penetrate the skin at the skin site. The transcutaneous device is mounted for movement between an initial position in which the transcutaneous device is retracted relative to the lower surface and an extended position in which the transcutaneous device projects relative to the lower surface, and for movement between the extended position and a retracted position (which may or may not be the same as the initial position) in which the transcutaneous device is retracted relative to the lower surface. The medical device further comprises an actuation means comprising a first user gripable portion moveable relative to the mounting surface, the first user gripable portion being moveable to cause the transcutaneous device to be moved from the initial position to the extended position, and a release means attached to a peripheral portion of the medical device and comprising a second user gripable portion moveable relative to the housing, the second user gripable portion being moveable to cause the transcutaneous device to be moved from the extended position to the retracted position, the release member further allowing a pulling force to be applied to the peripheral portion of the medical device to thereby remove the medical device when secured to the skin site, wherein in an initial state the first user gripable portion at least partially covers the second user gripable portion, such that the second user gripable portion is exposed when the first user gripable portion is moved to cause the transcutaneous device to be moved from the initial position to the extended position.

According to another aspect of the present invention, a medical device is provided comprising a mounting surface adapted for application towards a skin site, a transcutaneous device adapted to penetrate the skin at the skin site, the transcutaneous device being mounted for movement between an initial position in which the transcutaneous device is retracted relative to the lower surface and an extended position in which the transcutaneous device projects relative to the lower surface, and for movement between the extended position and a retracted position in which the transcutaneous device is retracted relative to the lower surface. The medical device further comprises actuation means including a first user actuatable portion being actuatable to cause the transcutaneous device to be moved from the initial position to the extended position, and release means including a second user actuatable portion actuatable to cause the transcutaneous device to be moved from the extended position to the retracted position, wherein the release means cannot be actuated before the actuation means has been actuated. Prevention of actuation of the release means may be provided by a mechanical lock released when actuation means is actuated, or the actuation means in its initial state may cover a portion of the release means, e.g. as disclosed above.

For all of the above embodiments in which a fluid communication is established between a transcutaneous device and a reservoir, this may be provided either via a direct connection between the transcutaneous device and the reservoir (e.g. by penetrating a septum of the reservoir) or indirectly (e.g. via connection to a structure in flow communication with the reservoir, e.g. the outlet of a suction pump drawing drug from a reservoir).

In order to provide a skin mountable medical device, e.g. of the above-discussed types, with an extended operational life, the medical device may be attached to a base plate unit comprising a mounting surface with means having an adhesive surface, the medical device and the base plate unit comprising mating, releasable coupling means allowing the medical device to be secured to the base plate unit a given number of times. The medical device may be a unitary drug delivery device or a unitary sensor device, or it may be a modular device comprising e.g. a pump unit and a needle unit or a sensor unit and a skin-penetrating sensor needle.

To extend the operational life of a medical device comprising an adhesive mounting surface, it may be provided with a first peelable sheet having an upper surface and an adhesive lower surface, the upper surface being adapted for peelable attachment to the adhesive surface of the mounting surface. Advantageously, at least one further peelable sheet is provided, each further peelable sheet comprising an upper surface and an adhesive lower surface, the first and the further peelable sheets being arranged in a stacked arrangement with their respective upper surfaces attached to the overlying adhesive surface. Indeed, such a stack may be used in combination either with a skin mountable medical device comprising an adhesive mounting surface or in combination with a base plate unit as described above.

To extend the operational life of a skin-mountable medical device comprising a transcutaneous device, the latter may be chosen to allow a relatively long period of placement through the skin at a given location. For a skin-mountable infusion set adapted for connection to a drug delivery device, and recently also in a skin-mountable drug delivery device comprising a build-in transcutaneous device, a soft polymeric cannula (e.g. made from Teflon®) in combination with an insertion needle is used as an alternative to a traditional steel needle. Although the soft cannula is used primarily for providing a high degree of wearing comfort, it is believed that this kind of cannalu also provides an extended wear time which may be attributed to the smooth surface of the polymeric material which may discourage infectious agents from adhering to and grove on the cannula surface. However, the soft cannulas have larger outer diameters, are longer and are more complex to insert as requiring an insertion needle, thus giving a traditional steel needle a number of advantages.

Thus, combining the above, the present invention provides in a further aspect, a medical device comprising a mounting surface adapted for application to a skin site, an adhesive for securing the mounting surface to the skin site, a transcutaneous device adapted to penetrate the skin at the skin site, wherein the transcutaneous device is in the form of a hollow metallic needle comprising an outer smooth coating of a polymeric material, e.g. PCTFE. The needle may be mounted for movement between an initial position in which the transcutaneous device is retracted relative to the lower surface and an extended position in which the transcutaneous device projects relative to the lower surface, and for movement between the extended position and a retracted position in which the transcutaneous device is retracted relative to the lower surface as described above. Correspondingly, the medical device may also be provided with the above described actuation and release means.

As used herein, the term "drug" is meant to encompass any drug-containing flowable medicine capable of being passed through a delivery means such as a hollow needle in a controlled manner, such as a liquid, solution, gel or fine suspension. Representative drugs include pharmaceuticals such as peptides, proteins, and hormones, biologically derived or active agents, hormonal and gene based agents, nutritional formulas and other substances in both solid (dispensed) or liquid form. Correspondingly, the term "subcutaneous infusion" is meant to encompass any method in which a needle device is inserted at a selected site within the body of a patient for subcutaneous, intravenous, intramuscular or intradermal delivery of a drug to a subject. Further, the term needle or needle device (when not otherwise specified) defines a piercing member (including an array of micro needles) adapted to be introduced into or through the skin of a subject.

The means defined in any claims can be performed by the following exemplary structures:

Attaching means: "attaching means in the form of the adhesive sheet", "attaching means in the form of the coupling means from the pump unit", "the attaching means being adhesive means (270) provided on the mounting surface", "attaching means comprises a sheet member (270) having an upper surface connected to the lower surface of the medical device, and a lower adhesive surface", "attaching means (141, 161) is adapted for securing the medical device to the pump unit and thereby relative to the skin of the subject."

Release means: "the release means responsible for providing the specified functionality may be provided by any suitable structure such as a release, a release member or a release assembly. These structures may be formed by of one or more components, which may be formed integrally, attached to each other or constituting an assembly or structure of functionally interrelated components and members which engage with each other but need not be connected to each other", "the release means may comprise gripping means connected to a peripheral portion of the mounting surface", "the release means comprises transcutaneous device retraction means operatable between", "release means in the form of the tab", "release means in the form of the coupling means", "release means (550, 275, 162); the release member 550, tab member 275 are formed integrally with sheet.

Adhesive means: "the adhesive means (e.g. a layer of a medical grade adhesive)", "adhesive material which per se allows the device to be removed and re-mounted a number of times, however, alternatively it may be accomplished by using "renewable" adhesive means".

Transcutaneous device retraction means: "user-gripable retraction in the form of a second strip-member 22", "transcutaneous device retraction means (555, 280)" the retraction portion of a strip formed from a flexible material] forming a loop 555 arranged below the lower arm of the needle carrier, "FIGS. 24A and 24B show the delivery device 250, the figures showing the retraction member 280 and its relationship with the needle unit 200 and the pulling member 277 and tab 275. The needle retraction member is attached to the pulling member 277 and comprises a first hook member 281 adapted to engage the first hook member 236 on the needle unit when the latter is moved from its initial position to its extended position (see FIG. 24A), an upwardly sloping ramp surface 282 and a flexible arm with a second hook member 283".

Locking means: "locking means (527, 283);" flexible release arm 526 comprising a catch 527 supporting and arresting the lower arm in its first downwardly biased position, an upwardly sloping ramp surface 282 and a flexible arm with a second hook member 283.

Coupling means: "the coupling means preferably being of mechanical, interlocking nature", "user-actuatable male coupling means 40 in the form of a pair of resiliently arranged hook members adapted to cooperate with corresponding female coupling means on the reservoir unit", "user actuatable coupling means 511 allowing a reservoir unit to be attached to and released from the needle unit 505, the reservoir unit comprising corresponding mating coupling means 506", "mating coupling means 141, 161 on the pump unit respectively the needle unit", "mating coupling means 441, 461 on the pump unit respectively the needle unit".

Outlet means: "an outlet means allowing the transcutaneous device to be arranged in fluid communication with an interior of the reservoir", "outlet means in the form of a protruding needle penetratable septum 145", "outlet means (261)."

Expelling means: "expelling means in the form of an electronically controlled pump", "In FIGS. 27A-27E examples of expelling means suitable for use with the present invention are shown schematically", "electric motor 1030 which via a worm-gear arrangement 1031 drives the piston rod to expel drug from the cartridge", "gas generating means 1120 in fluid communication with the interior of the cartridge via conduit 1121 for driving the piston to expel drug from the cartridge", "osmotic engine 1220 in fluid communication with the interior of the cartridge via conduit 1221 for driving the piston to expel drug from the cartridge", "A spring 1340 is arranged to act on the piston to drive fluid from the first to the second reservoir thereby expelling drug from the flexible reservoir", "membrane pump is (in a situation of use) connected to a reservoir 1410 from which drug is sucked through the pump and expelled through the outlet".

Mounting means: "mounting means (470) having an adhesive surface."

Actuation means: "an actuation means comprising a first user gripable portion moveable relative to the mounting surface", "actuation means including a first user actuatable portion being actuatable to cause the transcutaneous device to be moved from the initial position to the extended position, and release means including a second user actuatable portion actuatable to cause the transcutaneous device to be moved from the extended position to the retracted position", "usergripable actuation means in the form of a first strip-member 21", "The control and actuation means comprises a pump actuating member in the form of a lever and piston arrangement 481 driven by a coil actuator 482", "The needle unit further comprises needle actuation means whereby the needle can be moved between an initial position in which the needle is retracted relative to the lower surface of the needle unit and an extended position in which the needle projects through the aperture 121", "actuation means (540)," see actuation member 540 (see FIG. 14).

BRIEF DESCRIPTION OF THE DRAWINGS

In the following the invention will be further described with references to the drawings, wherein FIG. 19 shows in an exploded perspective view a reservoir unit.

When appropriate, in the figures like structures are identified by like reference numerals.

DESCRIPTION OF EXEMPLARY EMBODIMENTS

When in the following terms as "upper" and "lower", "right" and "left", "horizontal" and "vertical" or similar relative expressions are used, these only refer to the appended figures and not to an actual situation of use. The shown figures are schematic representations for which reason the configuration of the different structures as well as there relative dimensions are intended to serve illustrative purposes only.

Firstly, with reference to FIGS. 1-12 an embodiment of a drug delivery device will be described focusing primarily on the directly user-oriented features. The transcutaneous device unit 2 comprises a transcutaneous device in the form of a hollow infusion needle and will thus in the following be termed a needle unit, however, the needle may be replaced with any desirable transcutaneous device suitable for delivery of a fluid drug.

Figure 1:
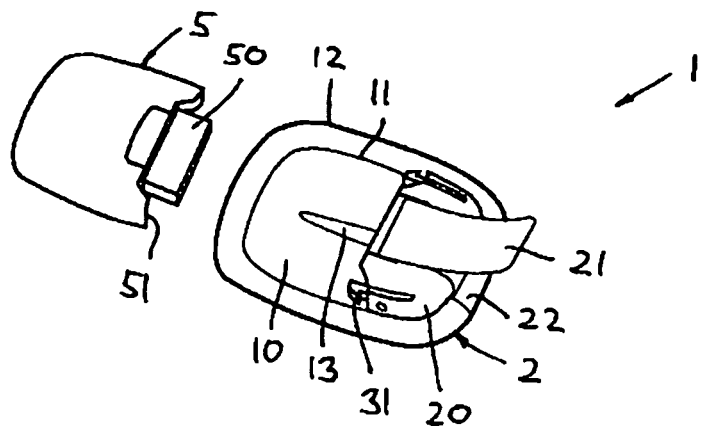
FIGS. 1-11 shows in perspective views the sequences of use for a first embodiment of a drug delivery device.

More specifically, FIG. 1 shows a perspective view of medical device in the form of a modular skin-mountable drug delivery device 1 comprising a patch-like needle unit 2 and a reservoir unit 5. When supplied to the user each of the units are preferably enclosed in its own sealed package (not shown).

The needle unit comprises a base portion 10 with a lower mounting surface adapted for application to the skin of a user, and a housing portion 20 in which a hollow infusion needle (not shown) is arranged. The needle comprises a first needle portion having a pointed distal end adapted to penetrate the skin of a user, and a second pointed end adapted to be arranged in fluid communication with the reservoir unit. In the shown embodiment the pointed end of the needle is moveable between an initial position in which the pointed end is retracted relative to the mounting surface, and an extended position in which the pointed end projects relative to the mounting surface. Further, the needle is moveable between the extended position in which the pointed end projects relative to the mounting surface, and a retracted position in which the pointed end is retracted relative to the mounting surface. The needle unit further comprises user-gripable actuation means in the form of a first strip-member 21 for moving the pointed end of the needle between the initial and the second position when the actuation means is actuated, and user-gripable retraction in the form of a second strip-member 22 means for moving the pointed end of the needle between the extended and the retracted position when the retraction means is actuated. As can be seen, the second strip is initially covered by the first strip. The housing further comprises user-actuatable male coupling means 40 in the form of a pair of resiliently arranged hook members adapted to cooperate with corresponding female coupling means on the reservoir unit, this allowing the reservoir unit to be releasable secured to the needle unit in the situation of use. In the shown embodiment the base portion comprises a relatively rigid upper portion 11 attached to a more flexible adhesive sheet member 12 having a lower adhesive surface providing the mounting surface per se, the adhesive surface being supplied with a peelable protective sheet. The base portion also comprises a ridge member 13 adapted to engage a corresponding groove on the reservoir unit.

The reservoir unit 5 comprises a pre-filled reservoir containing a liquid drug formulation (e.g. insulin) and expelling means in the form of an electronically controlled pump for expelling the drug from the reservoir through the needle in a situation of use. The reservoir unit has a generally flat lower surface adapted to be mounted onto the upper surface of the base portion, and comprises a protruding portion 50 adapted to be received in a corresponding cavity of the housing portion 20 as well as female coupling means 51 adapted to engage the corresponding hook members 31 on the needle unit. The protruding portion provides the interface between the two units and comprises a pump outlet and contact means (not shown) allowing the pump to be started as the two units are assembled. The lower surface also comprises a window (not to be seen) allowing the user to visually control the contents of the reservoir.

Figure 2:
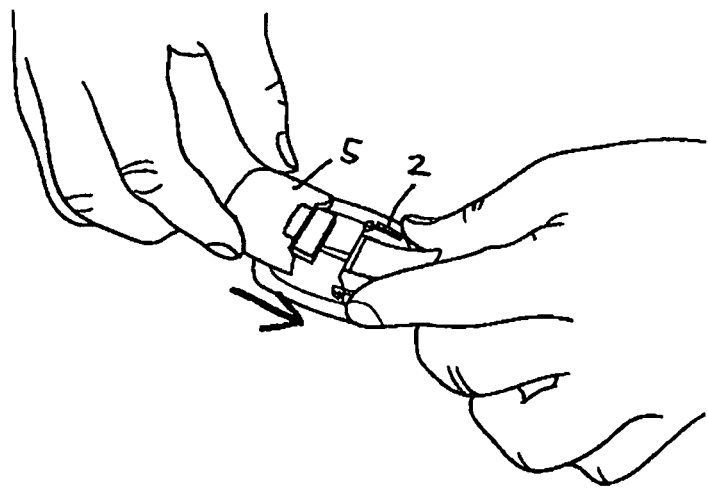
Figure 3:
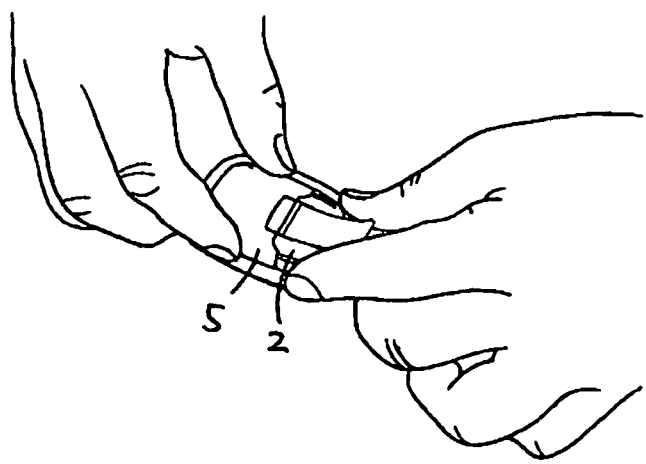
Figure 4:
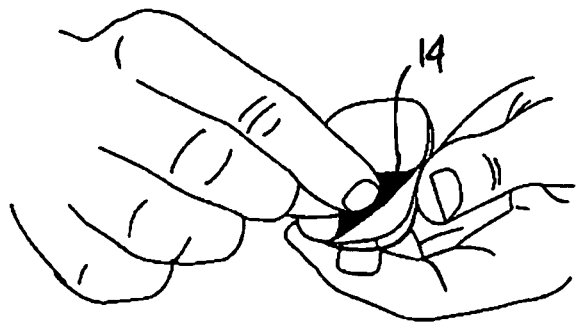
Figure 5:
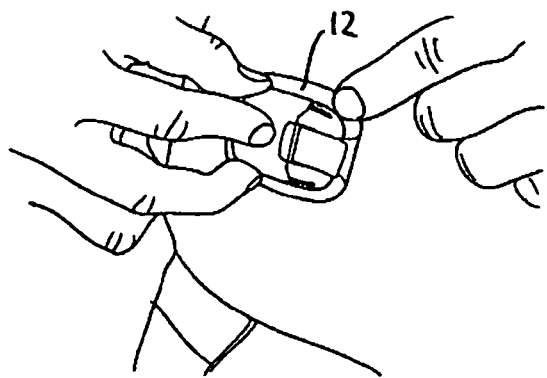
Figure 6:
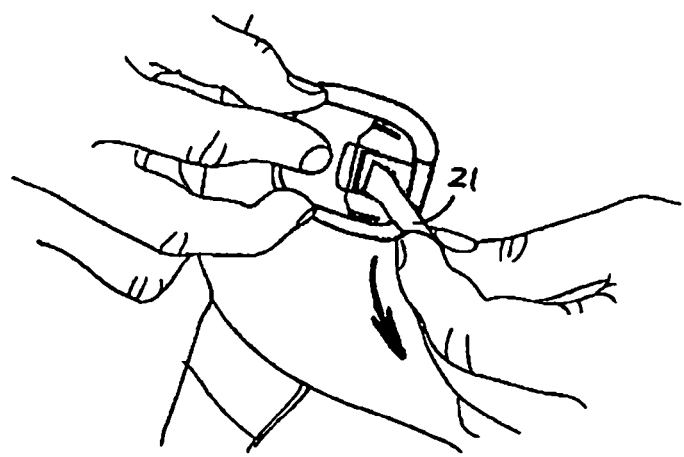
Figure 7:
Figure 8:
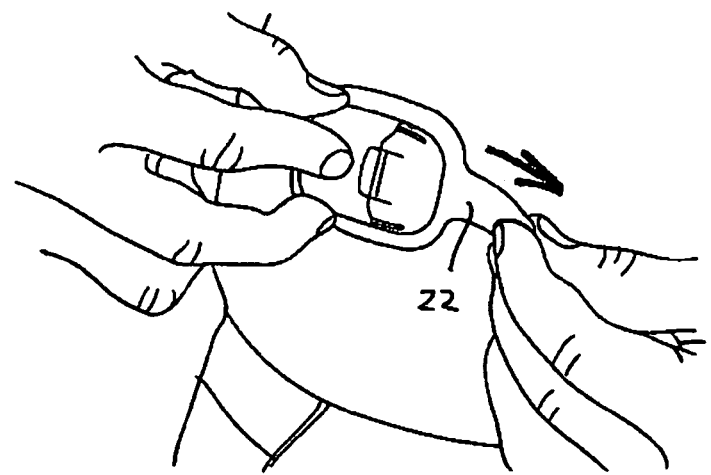

First step in the mounting procedure is to assemble the two units by simply sliding the reservoir unit into engagement with the needle unit (FIG. 2). When the hook members properly engage gage the reservoir unit a "click" sound is heard (FIG. 3) signalling to the user that the two units have been properly assembled. If desired, a visual or audible signal may also be generated. Thereafter the user removes the peelable sheet 14 to uncover the adhesive surface (FIG. 4) where after the device can be attached to a skin surface of the user, typically the abdomen (FIG. 5). Infusion of drug is started by gripping and pulling away the actuation strip 21 as indicated by the arrow whereby the needle is inserted followed by automatic start of the infusion (FIG. 6). The needle insertion mechanism may be supplied in a pre-stressed state and subsequently released by the actuation means or the needle insertion may be "energized" by the user. A "beep" signal confirms that the device is operating and drug is infused. The reservoir unit is preferably provided with signal means and detection means providing the user with an audible alarm signal in case of e.g. occlusion, pump failure or end of content.

Figure 9:
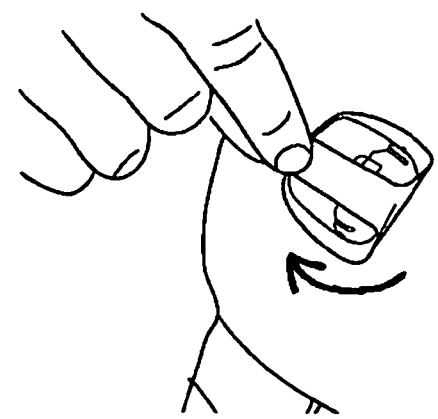
Figure 10:
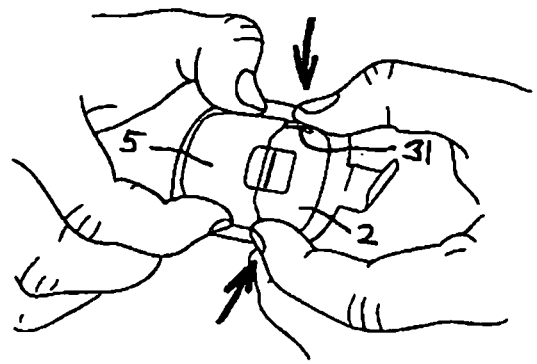
Figure 11:
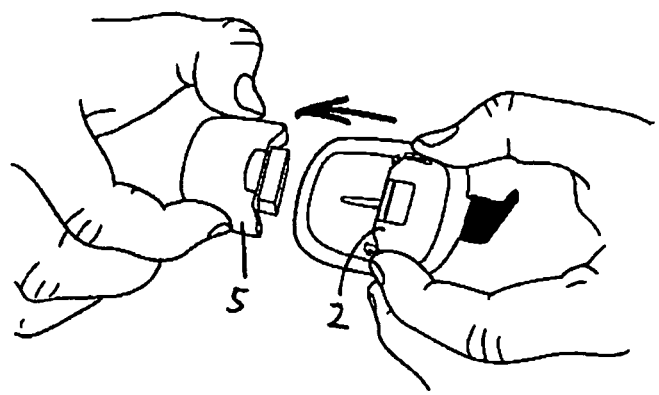
Figure 12:
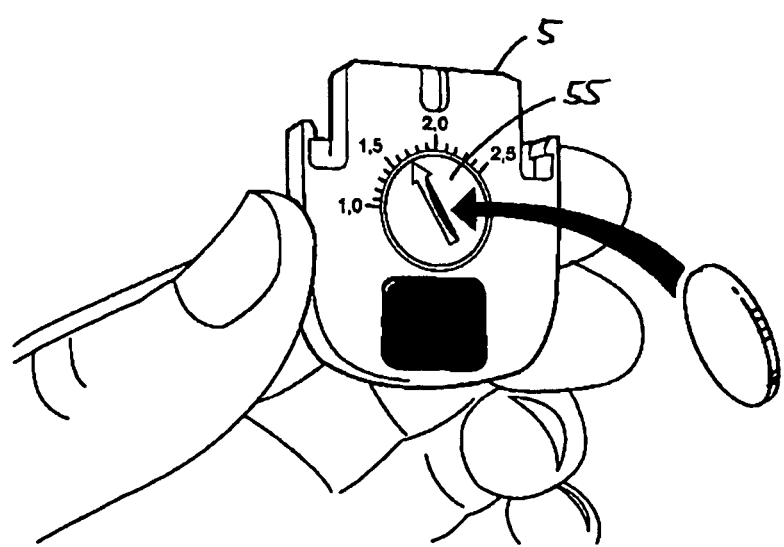
FIG. 12 shows a further embodiment of a reservoir unit.

After the device has been left in place for the recommended period of time for use of the needle unit (e.g. 48 hours) —or in case the reservoir runs empty or for other reasons—it is removed from the skin by gripping (FIG. 7) and pulling (FIG. 8) the retraction strip 22 as indicated by the arrows which leads to retraction of the needle followed by automatic stop of drug infusion where after the strip which is attached to the adhesive patch is used to remove the device from the skin surface (FIG. 9).

When the device has been removed the two units are disengaged by simultaneously depressing the two hook members 31 as indicated by the arrows (FIG. 10) allowing the reservoir unit 5 to be pulled out of engagement with the needle unit 2 as indicated by the arrow (FIG. 11) which can then be discarded. Thereafter the reservoir unit can be used again with fresh needle units until it has been emptied.

The reservoir unit may be supplied with a fixed basal infusion rate or it may be supplied as an adjustable unit (FIG. 12) with adjustment means 55 allowing the infusion rate to be set by a physician and/or the user/patient. The reservoir unit may also be provided with means allowing the control means to be programmed or set electronically (not shown).

The device described with reference to FIGS. 1-11 may also be used in alternative ways. For example, the needle unit may be mounted to the skin after which the reservoir is attached. Depending on the configuration of the needle unit, it may be possible or prevented that the needle is introduced before the reservoir unit is attached.

Figure 13:
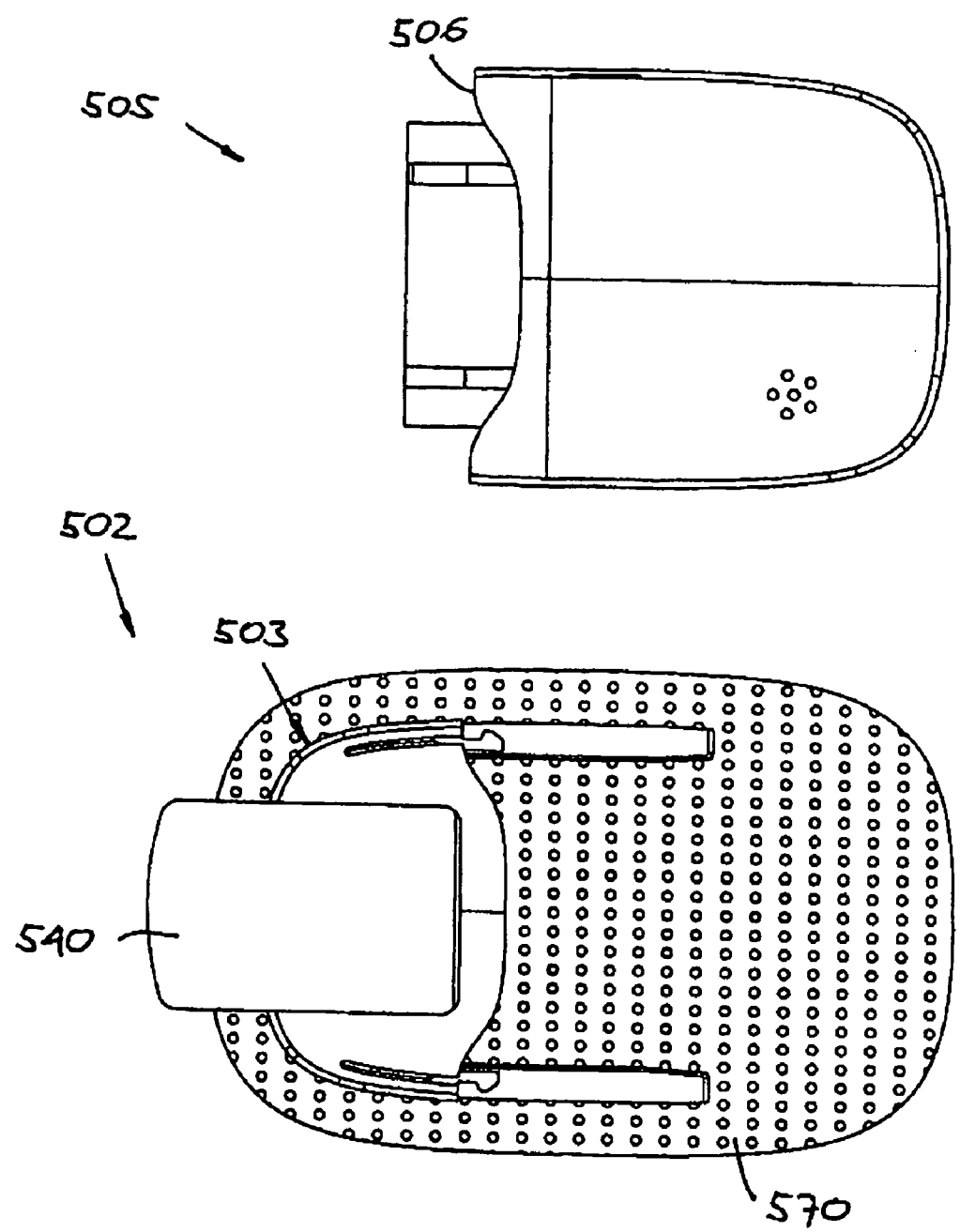
FIG. 13 shows in a non-assembled state a needle unit and a reservoir unit for a further embodiment of a drug delivery device.

FIG. 13 shows a further embodiment of medical device 500 substantially corresponding to the embodiment of FIG. 1, the device comprising a patch-like needle unit 502 and a thereto attachable reservoir unit 505.

Figure 14:
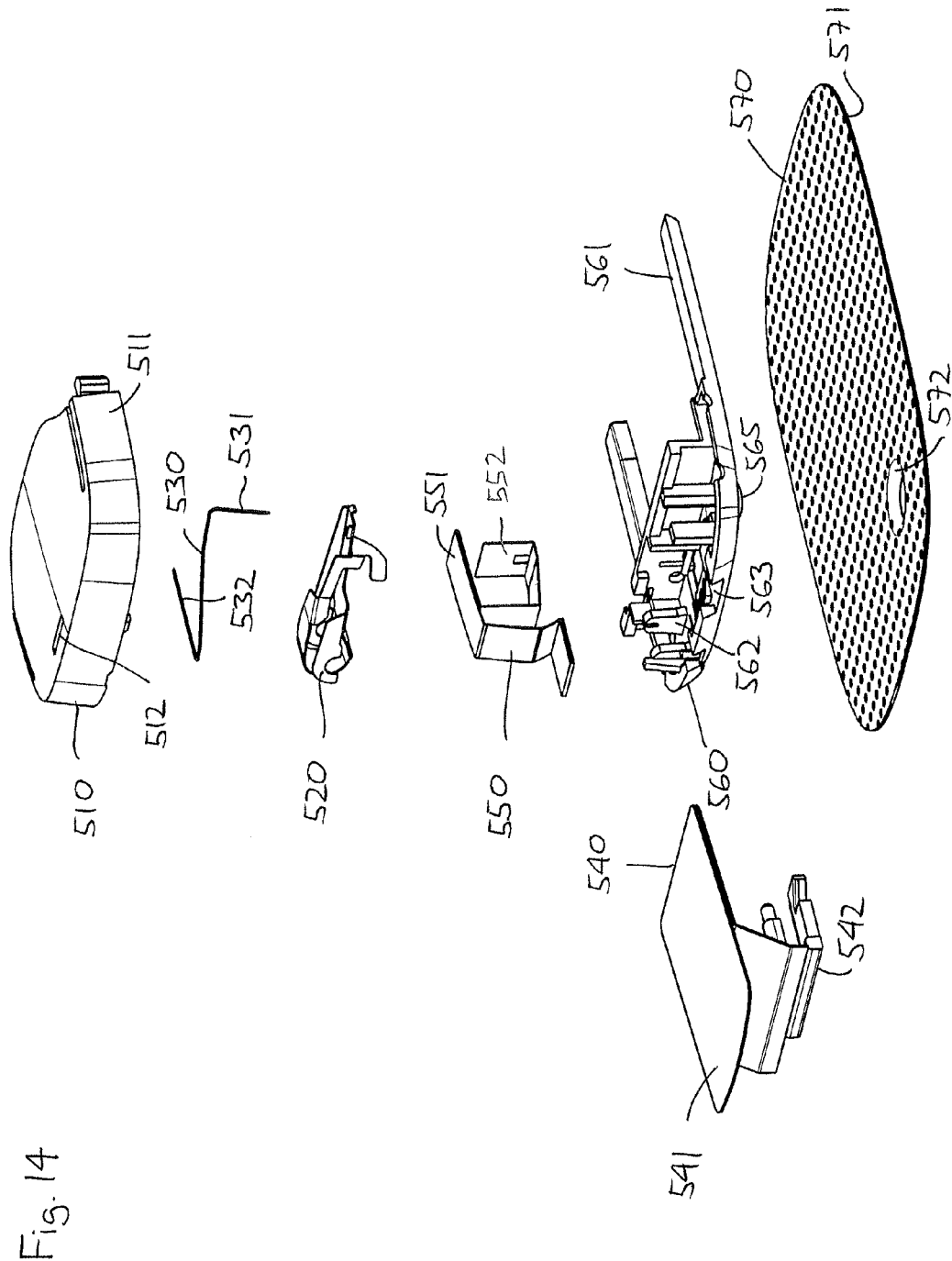
FIG. 14 shows an exploded view of the needle unit of FIG. 13.
Figure 15:
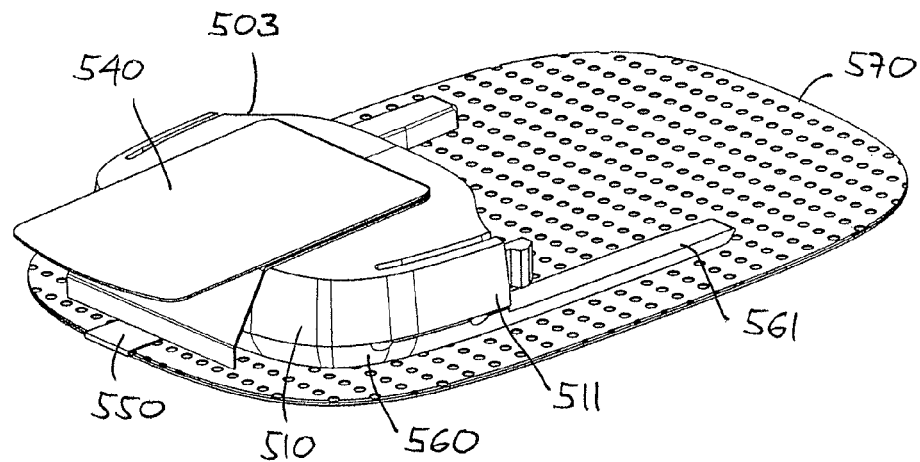
FIG. 15 shows a perspective view of the needle unit of FIG. 13 in a first state.

FIG. 14 shows an exploded perspective view of the needle unit comprising an upper housing portion 510, a needle carrier 520 and a thereto mounted infusion needle 530, an actuation member 540, a release member 550, a lower housing portion 560 and a sheet member 570. The actuation member comprises a user gripable portion 541 and a needle actuation portion 542, and the release member comprises a user gripable portion 551 and a needle retraction portion 552. In the assembled state as shown in FIG. 15, the upper and lower housing portions form a housing 503 in which the needle and the needle carrier is mounted, the actuation and release members being operatable connected to the needle carrier with the user gripable portions arranged outside the housing. In contrast to the FIG. 1 embodiment does the needle unit not comprise a base plate portion but instead two ridge members 561 extending from the housing, the ridge members and the lower surface of the housing being mounted on the flexible sheet member which is provided with a lower adhesive layer 571 on its lower surface allowing the needle unit to be attached to a skin site of a subject. The sheet member further comprises an opening 572 arranged in register with a lower protrusion 565 provided around the exit aperture for the transcutaneous device, just as the sheet is provided with a large number of small perforations to improve breathability through the sheet. The housing 503 is provided with user actuatable coupling means 511 allowing a reservoir unit to be attached to and released from the needle unit 505, the reservoir unit comprising corresponding mating coupling means 506.

As seen is the user gripable portion 551 of the release member initially covered by a portion of the actuation member, this reducing the probability that the user erroneously uses the release member instead of the actuation member. Further, the actuation and release members (or portion thereof) may be colour coded to further assist the user to correctly use the device. For example, the actuation member may be green to indicate "start" whereas the release member may be red to indicate "stop".

Figure 16:
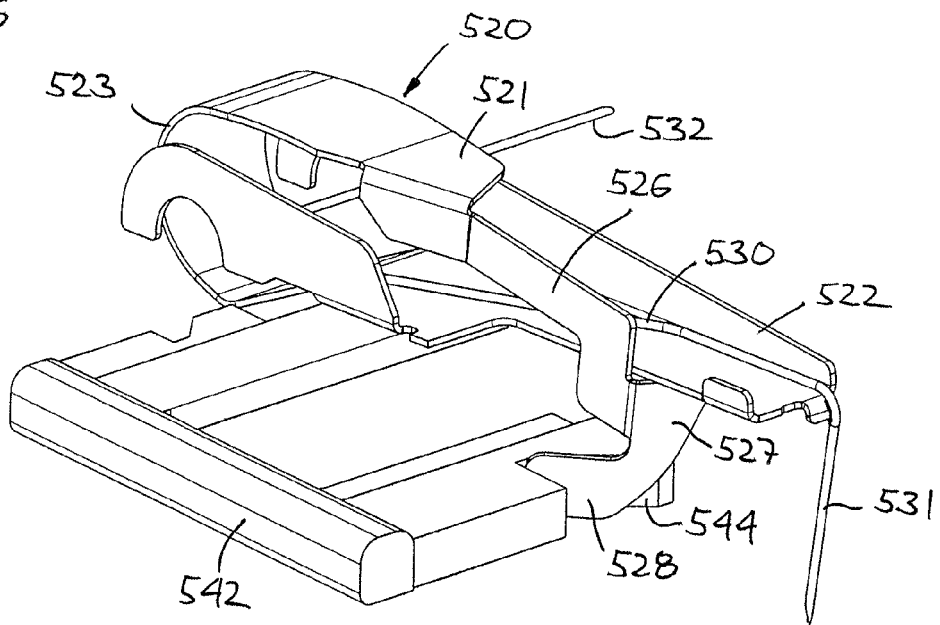
FIG. 16 shows a perspective view of the needle carrier of FIG. 14.

FIG. 16 shows in perspective the needle carrier 520 with the needle 530 and the needle actuation portion 542 of the actuation member 540. The needle actuation portion comprises two legs allowing it to slide relative to the housing, the legs being arranged through respective openings 563 in the housing. The needle carrier is adapted to be connected to a hinge member 562 of the lower housing portion to thereby allow the needle carrier and thereby the needle to pivot corresponding to a pivoting axis defined by a hinge. In the shown embodiment is the needle carrier in the form a bent sheet metal member, the carrier comprising an upper arm 521 and a lower arm 522 connected to each other by a hinge portion 523 allowing the lower arm to pivot relative to the upper arm and corresponding to the pivoting axis. The lower arm forms a tray in which the hollow infusion needle 530 is mounted (e.g. by welding or adhesive), the needle having a distal pointed portion 531 adapted to penetrate the skin of the subject, the distal portion extending generally perpendicular to the mounting surface of the needle unit, and a proximal portion 532 arranged substantially corresponding to the pivoting axis and adapted to engage a fluid supply. Thus, when a portion of the upper arm is mounted in the housing, the lower arm can pivot between a first retracted position in which the distal portion of the needle is retracted within the housing, and a second extended position in which the distal portion projects relative to the mounting surface. In the shown embodiment the needle carrier provides the drive means for moving the lower arm between the two positions. This may as in the present embodiment be provided by the elastic properties of the sheet material per se corresponding to the hinge portion, or alternatively an additional spring may be provided between the two arms to thereby urge them apart. To lock the lower part in an energized, releasable first position, the upper arm is provided with a flexible release arm 526 comprising a catch 527 supporting and arresting the lower arm in its first downwardly biased position, as well as a release portion 528 engaging a ramp surface 544 of the needle actuation portion 542, the catch further comprising an inclined edge portion 529 adapted to engage the lower arm when the latter is moved from its extended to its retracted position as will be described in greater detail below.

Figure 17:
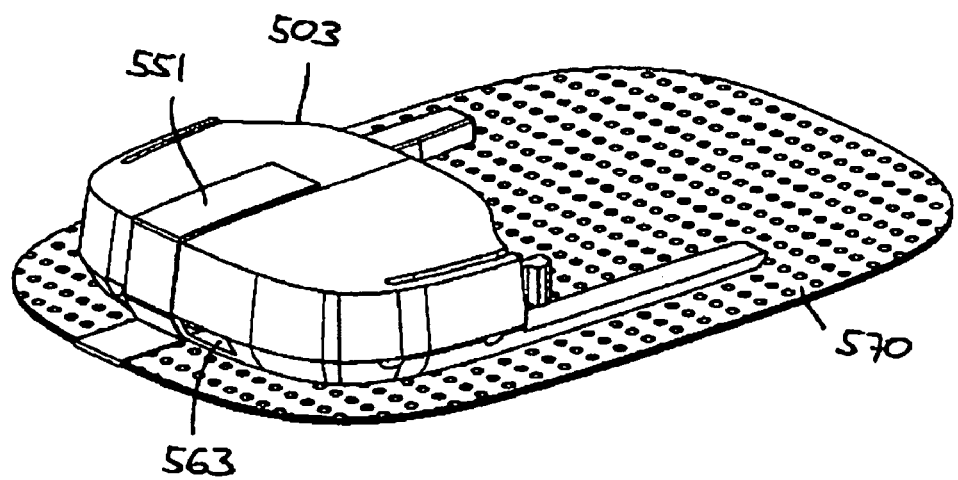
FIG. 17 shows a perspective view of the needle unit of FIG. 13 in a second state.

To actuate the needle the user grips the flexible strip forming the user gripable portion 541 (which preferably comprises adhesive portions to hold it in its shown folded initial position) and pulls the needle actuation portion 542 out of the housing, the actuation member 540 thereby fully disengaging the housing. More specifically, when the ramp surface 544 is moved it forces the catch 527 away from the lower arm to thereby release it, after which the release portion 528 disengages the ramp allowing the two legs to be pulled out of the housing. As seen in FIG. 17, when the actuation member is removed the user gripable portion 551 of the release member is exposed. As for the actuation member, the user gripable portion of the release member preferably comprises adhesive portions to hold it in its shown folded initial position.

Figure 18:
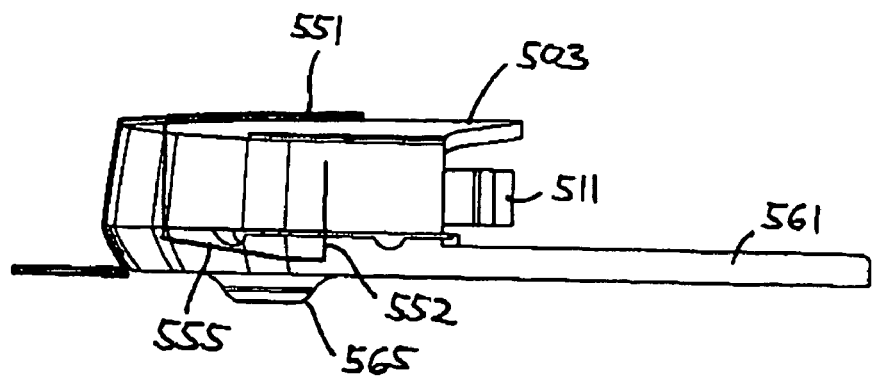
FIG. 18 shows a side view of the needle unit of FIG. 13.

In the shown embodiment the release member is in the form of a strip formed from a flexible material and having an inner and an outer end, the strip being threaded through an opening 512 in the housing, the strip thereby forming the user gripable portion 551 and the needle retraction portion 552, the inner end of the strip being attached to the housing and the outer end of the strip being attached to a peripheral portion of the sheet member 570 or, alternatively, a peripheral portion of the housing. In the projection shown in FIG. 18 the release member is shown in its initial position, the retraction portion forming a loop 555 arranged below the lower arm of the needle carrier, this position allowing the lower arm to be moved to its actuated position and thereby the needle to its extended position.

When the user decides to remove the needle unit from the skin, the user grips the user gripable portion 551, lifts it away from the housing and pulls it upwardly whereby the loop shortens thereby forcing the lower arm upwardly, this position corresponding to an intermediate release state. By this action the lower arm engages the inclined release portion 528 of the catch 527 thereby forcing it outwardly until it snaps back under the lower arm corresponding to the position shown in FIG. 16. As the actuation member 540 has been removed from the needle unit, the needle carrier is irreversibly locked in its retracted position. When the user further pulls in the release member, the peripheral portion of the sheet member to which the release member is attached will be lifted off the skin, whereby the needle unit with its attached reservoir unit can be removed from the skin, this as shown and described in FIGS. 7-9.

Advantageously, the actuation and release members may be formed and arranged to communicate with the reservoir unit (not shown). For example, one of the legs of the actuation member may in its initial position protrude through the housing to thereby engage a corresponding contact on the reservoir unit, this indicating to the reservoir unit that the needle unit has been attached, whereas removal of the actuation member will indicate that the needle has been inserted and thus that drug infusion can be started. Correspondingly, actuation of the release member can be used to stop the pump.

With reference to FIG. 19 an embodiment of a reservoir unit 405 of a type suitable to be used with the above described needle units is shown, the reservoir unit comprising a housing 451 in which a flexible reservoir 460, a pump unit 470 in the form of a mechanically actuated membrane pump, and control and actuation means therefore is arranged. The housing comprises a display 452 providing information to the user, e.g. the amount of drug left in the reservoir or information in respect of a malfunction condition. The control and actuation means comprises a pump actuating member in the form of a lever and piston arrangement 481 driven by a coil actuator 482, a microprocessor 483 for controlling the different functions of the reservoir unit, signal generating means 485 for generating an audible and/or tactile signal, and an energy source 486.

Figure 21A:
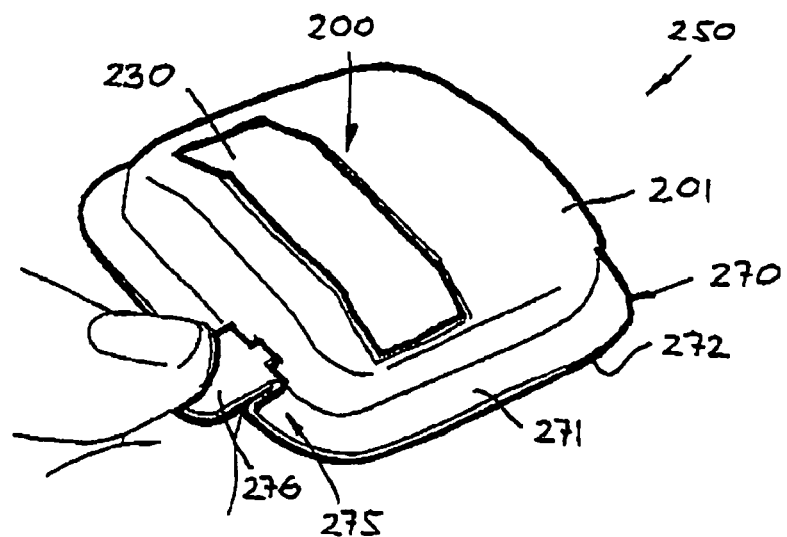
FIGS. 21A and 21B show in perspective views situations of use for a further embodiment of a drug delivery device.

FIG. 21A shows a perspective view of medical device in the form of a drug delivery device in accordance with an aspect of the invention. More specifically, FIG. 21A shows a drug delivery device 250 arranged on a skin surface of user and in a situation of use just prior to the user removing the device from the skin. The drug delivery device comprises a housing 201 with a lower surface attached to an upper surface 271 of a flexible sheet (or patch) 270, the sheet comprising a lower adhesive surface 272 allowing the device to be mounted on a skin surface of a user as shown. When supplied to the user, the adhesive surface is advantageously covered with a peelable release liner. The device further comprises a drug reservoir, a subcutaneous needle as well as expelling means (see below) for expelling the drug from the reservoir to the user via the subcutaneously arranged needle. The needle is arranged in a needle unit having a carrier 230 pivotally connected to the housing. Corresponding to the situation shown in FIG. 21A the needle is in an extended position with its pointed needle end inserted subcutaneously in the user. To protect the delivery device against accidental removal (e.g. during sleep or exercise) the sheet and its lower adhesive surface 272 is somewhat larger than the lower surface of the housing, the sheet thereby providing a border 273 around the device. The sheet also comprises a tab member 275 formed integrally with sheet. The tab is relative long allowing it to be folded in a zigzag configuration upon the border with only a short gripping portion 276 extending from the border, the gripping portion allowing the tab to be gripped by the use as shown.

Figure 21B:
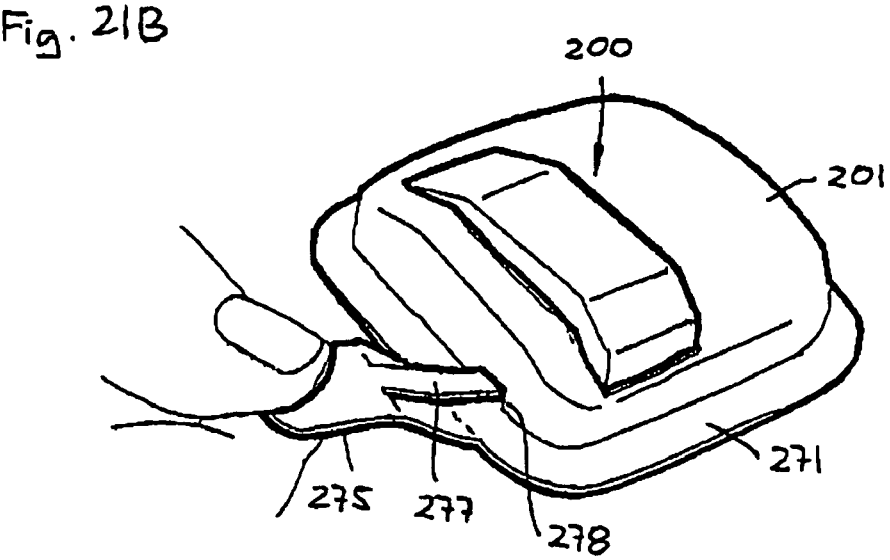

When the user intends to remove the delivery device from the skin surface, the user grips the gripping portion of the tab and pulls it in a first direction substantially in parallel with the skin surface, by which action the zigzag folded tab unfolds to its full length as shown in FIG. 21B. As also shown a pulling member in the form of a flexible strip 277 is attached at one end to the tab and at another end to a needle retraction member (see below) arranged within the housing, the pulling member extending through an opening 278 in the housing. As the tab is unfolded the pulling member is moved and the thereto attached retraction member pivots (or releases) the needle unit from an extended position in which the needle projects relative to the lower surface to a retracted position in which the needle is retracted relative to the lower surface, this as indicated by the carrier 230 being moved to a position in which it projects relative to the housing. When the needle has been withdrawn from the skin, the user uses the now unfolded tab to pull off the entire delivery device from the skin surface, for example by pulling the tab in a direction away from the skin surface (not shown).

As appears from the above, release means in the form of the tab has been operated from a first initial state (corresponding to FIG. 1A) through an intermediate state (corresponding to FIG. 21B) to a second state (not shown), whereby operation of the release means from the first to the intermediate state has caused the needle to be moved from an extended position to a retracted position, and operation of the release means from the intermediate to the second state has caused release of the attaching means in the form of the adhesive sheet from the skin surface.

As illustrated, the tab is moved in a first direction in parallel with the skin surface, however, as the strip 277 is flexible, the user may operate the tab also between the first and intermediate positions by pulling in a direction away from the skin surface, e.g. perpendicularly.

Figure 22A:
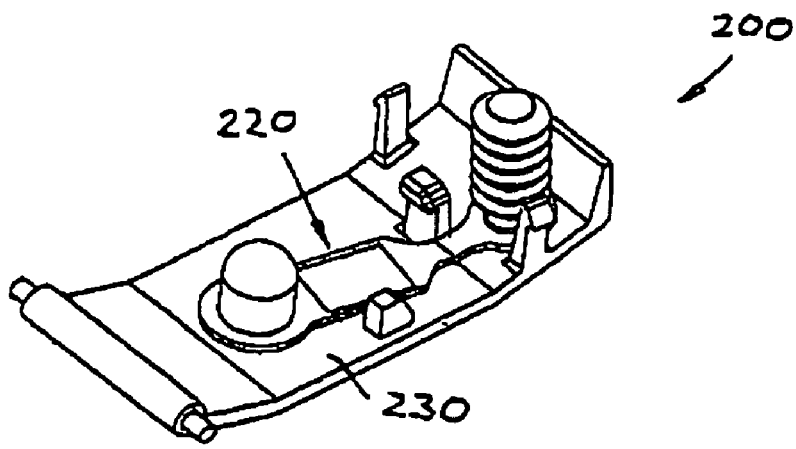
FIG. 22A shows a needle unit.
Figure 22B:
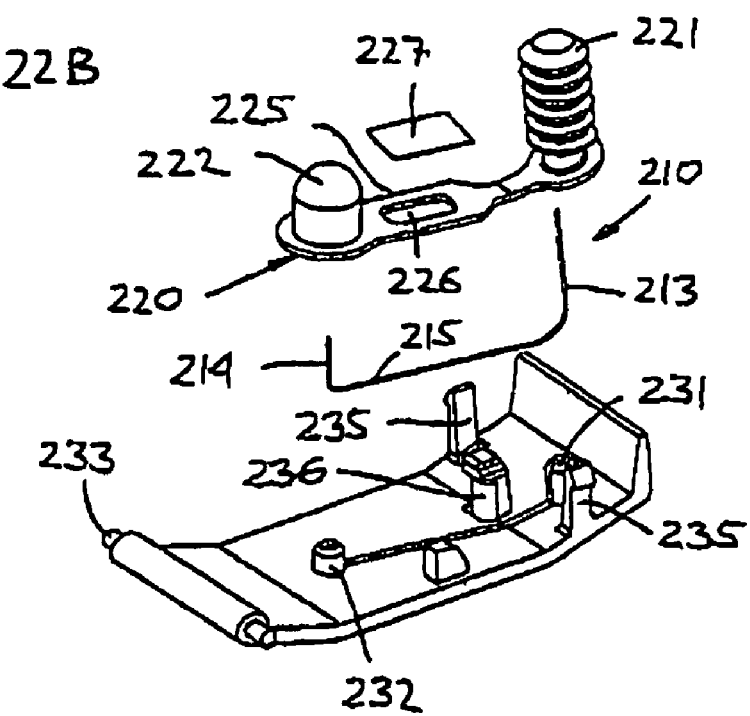
FIG. 22B shows an exploded view of the needle unit of FIG. 2A, FIGS. 23A and 23B show cross-sectionals view of the needle unit FIG. 22A mounted to a drug delivery device as shown in FIG. 21A, FIGS. 24A and 24B show in perspective partially cut-away views delivery devices corresponding to FIGS. 21A and 21B, FIGS. 25A and 25B show in perspective views situations of use a further embodiment of a drug delivery device.

Before turning to the description of the retraction mechanism, the needle unit 200 as shown in FIGS. 22A and 22B will be described. More specifically, FIG. 22A shows a needle unit 200 comprising a needle carrier 230 to which a U-formed needle 210 and a cover member 220 are attached. The needle comprises a first needle portion 213 having a first pointed end adapted to penetrate the skin of a subject, and a second needle portion 214 in fluid communication with the first needle portion via an intermediate needle portion 215 and having a second pointed end, the two needle portion being arranged substantially in parallel with each other corresponding to the legs of the U-formed needle. The carrier comprises gripping means 231, 232 for holding the needle, hinge means 233 allowing the needle unit to be pivotally connected to a delivery device, and first and second hook members 236, 235 intended for engagement with the delivery device (see below).

The cover member is made from a deformable elastic or non-elastic material and comprises first and second collapsible cover portions 221, 222 encapsulating the first respectively the second needle portions, the cover portions being collapsible from an initial configuration surrounding the needle portions to a collapsed configuration (e.g. in the form of an elastic rubber cover as shown or a telescoping arrangement) wherein the needle portions extend through the cover portions (see below). In the shown embodiment the cover portions are in the form of a bellows and a rounded cylinder, however, they may have any configuration allowing them to collapse. The two cover portions are connected by an intermediate portion 225 which in combination with the carrier forms a conduit providing fluid communication between the first and second enclosures formed by the two cover portions, the intermediate portion comprising a window 226 closed by a paper sheet 227. The paper sheet is penetratable to sterilizing gases (e.g. water vapour or ethylene gas) yet provides a sterility barrier for the encapsulated, this allowing sterilization of the enclosed needle.

Although not essential for the present invention, the needle may be mounted for movement between an initial position in which the needle is retracted relative to the lower surface allowing the delivery device to be handled and mounted on a skin surface without the needle projecting from the lower surface thereof, and an extended position in which the needle projects relative to the lower surface thus allowing a drug to be delivered, this as corresponding to the FIG. 21A situation.

Correspondingly, FIGS. 23A and 23B show partial cross-sectionals view of the needle unit 200 incorporated in the drug delivery device 250. For illustrative purposes, the sheet member 270 is not shown. The drug delivery device comprises a base plate 251 with a lower skin mountabale surface 252 and an aperture 253, a housing member 255 forming a secondary reservoir 256 containing a drive fluid (see description of the FIG. 27D embodiment below) and in which a flexible, bag-like drug reservoir 260 is arranged, the drug reservoir comprising a needle-penetratable elastomeric septum 261. The needle unit is pivotally connected to the housing member corresponding to a hinge 234, the carrier 230 thereby forming a lid member. In the shown embodiment the lid member is part of a relatively small needle unit, however, the lid may also be formed integrally with the housing member, the two portions being connected by e.g. a film hinge, in which case the needle unit would incorporate a portion of the drug delivery device.

FIG. 23A shows the delivery device in an initial state in which both of the needle portions 213, 214 are sterilely enclosed within the collapsible cover portions 221, 222. FIG. 23B shows the delivery in a state of use in which the lid has been moved into locking engagement with the needle retraction member by means of the hook member 236 (see below). During this operation the first needle portions is moved through the aperture in the base plate, thereby penetrating the skin of the user when the delivery device has been mounted on a skin surface, and the second needle portion penetrates the reservoir septum to thereby establish fluid communication between the reservoir and the needle. As appears from the figure, during this operation the cover portions 221, 222 collapses as they are moved into engagement with the base plate respectively the septum, the pointed needle portions thereby penetrating the covers. After use the movement of the needle unit is reversed to thereby withdraw the used needle into the device and de-connect the needle from the reservoir to thereby stop the flow and/or prevent leakage.

Figure 24A:
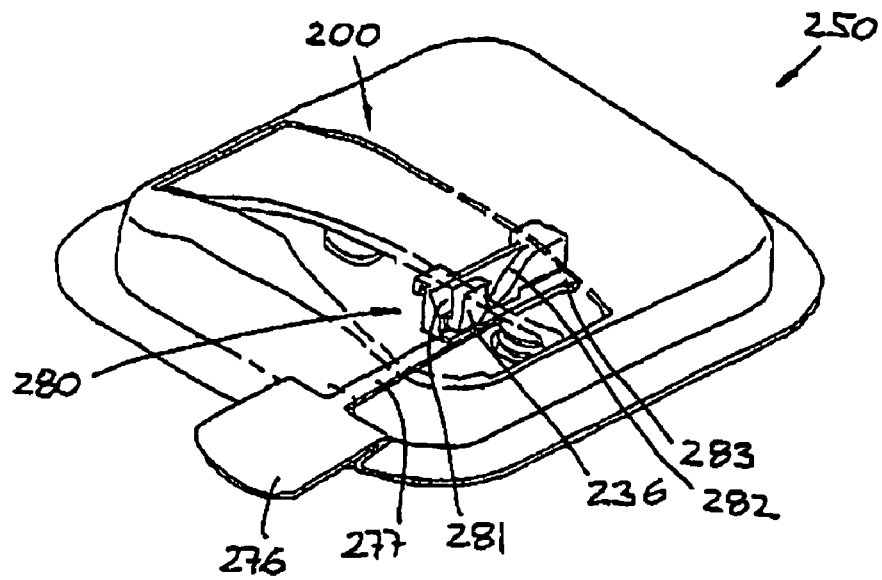
Figure 24B:
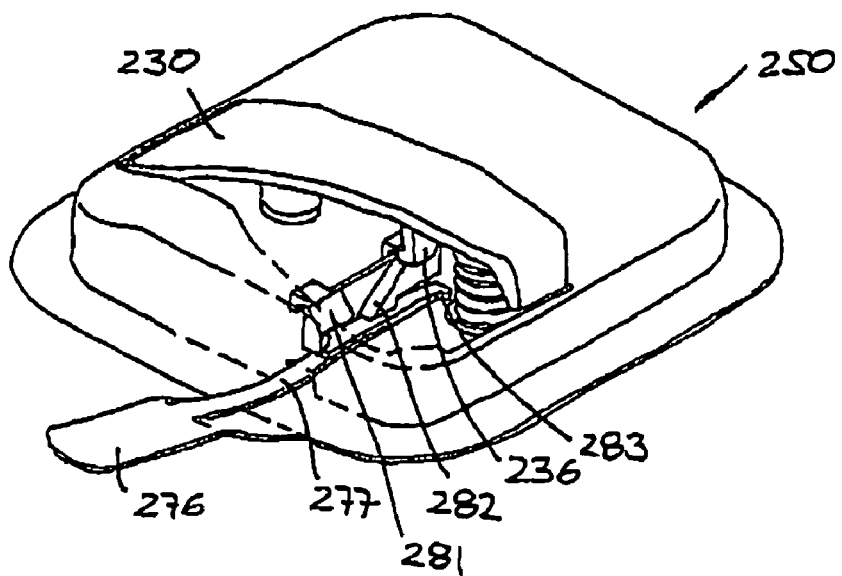

FIGS. 24A and 24B show the delivery device 250 in the same situations of use as shown in FIGS. 1A and 1B respectively, the figures showing the retraction member 280 and its relationship with the needle unit 200 and the pulling member 277 and tab 275. More specifically, the needle retraction member is operatable between a first position in which the needle projects relative to the lower surface and a second position in which the needle is retracted relative to the lower surface, wherein the needle retraction member is moved between its first and second positions when the tab and the pulling member is operated between the first and intermediate states as described above.

The needle retraction member is attached to the pulling member 277 and comprises a first hook member 281 adapted to engage the first hook member 236 on the needle unit when the latter is moved from its initial position to its extended position (see FIG. 24A), an upwardly sloping ramp surface 282 and a flexible arm with a second hook member 283. When the user operates the tab from its initial folded configuration to its extended configuration (see FIG. 24A) the pulling member moves the retraction member from its first to its second position, whereby the first hook member 236 of the needle unit first disengages the first hook member 281 on the retraction member and thereafter slides upwardly on the ramp thereby pivoting the needle unit to its retracted position, and the second hook member 283 engages a mating structure (not shown) of the delivery device thereby locking the retraction member in its second position. To prevent the needle unit from pivoting further upwardly the second hook members 235 on the carrier (see FIG. 22B) engages the housing whereby the needle unit is securely locked in its retracted position. To prevent accidental withdrawal of the needle during use, the needle retraction member advantageously is arranged such that a given resistance has to be overcome in order to move the retraction member from its first to its second position, e.g. by using the hook member 283 to releasably lock the retraction member in its first position.

With reference to FIGS. 21-24 a unitary delivery device has been described in which the inserted needle is retracted before the skin-mountable delivery device is detached from the skin of the user, however, the principles of the present invention may also be implied in other configurations.

Figure 25A:
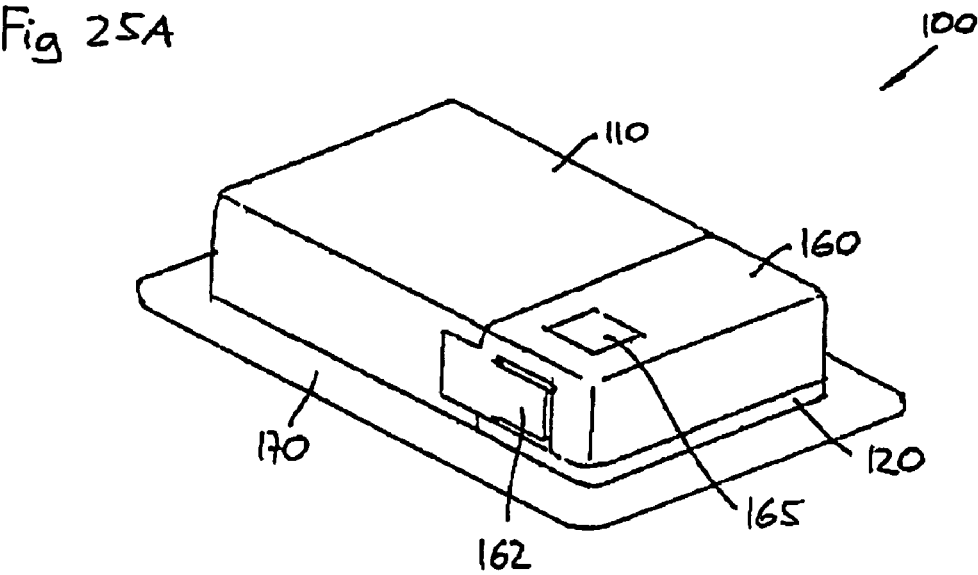
FIGS. 25C and 25D show in perspective views further embodiments of a drug delivery device.
Figure 25B:
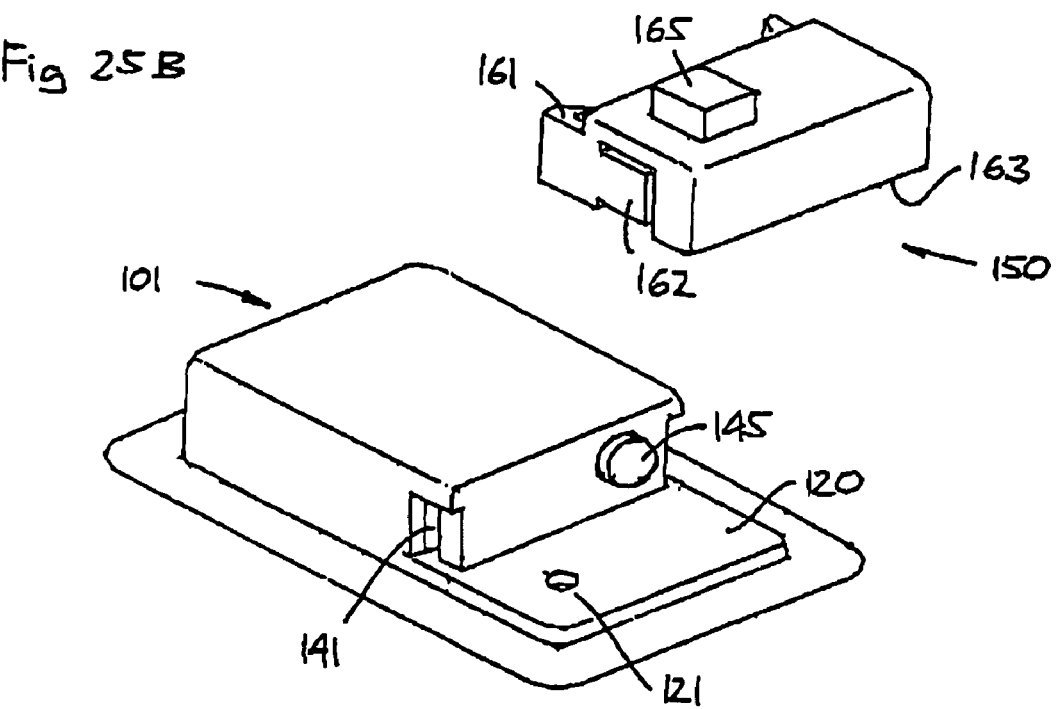

Correspondingly, with reference to FIGS. 25A and 25B a second embodiment of a drug delivery device will be disclosed in which a separate needle unit is releasably attached to a skin-mountable pump unit. The pump unit is adapted to be mounted on the skin of a user and used for a given number of days during which the delivery needle can be exchanged any desired number of times.

More specifically, the delivery device 100 comprises a skin-mountable pump unit 101 to which a needle unit 150 is releasable attached. The pump unit comprises a housing portion 110, in which a reservoir and expelling means are arranged, and from which a base plate portion 120 with an aperture 121 extends, the housing and the base plate portions forming a common lower surface arranged on a flexible adhesive patch member 170 comprising a lower adhesive surface allowing the pump unit to be mounted on the skin of a user, the upper surface of the base plate portion and the adjacent part of the housing portion forming a receiving portion for the needle unit. When supplied to the user, the adhesive surface is advantageously covered with a peelable release liner. The reservoir is adapted to contain a liquid drug (e.g. prefilled or adapted to be filled by a user) and comprises an outlet means in the form of a protruding needle penetratable septum 145 adapted to be arranged in fluid communication with the second needle portion (see below). The expelling means (not shown) is adapted for in a situation of use to expel a drug out of the reservoir and through the skin of the subject via a hollow needle. The reservoir and expelling means may be of any suitable configuration, e.g. as disclosed with reference to FIGS. 27A-27D.

The needle unit 150 comprises a housing 160 having a lower surface 163 and a moveable delivery needle arranged there within (see below). The needle unit is configured to be mounted on the upper surface of the base plate portion 120 and in engagement with the housing portion by means of mating coupling means 141, 161 on the pump unit respectively the needle unit. The needle unit further comprises needle actuation means whereby the needle can be moved between an initial position in which the needle is retracted relative to the lower surface of the needle unit and an extended position in which the needle projects through the aperture 121. Preferably the needle is prevented from being moved to its extended position until the needle unit has been properly engaged with the pump unit, this to prevent unintended needle sticks. The needle may be actuated automatically when it is attached to the pump unit or manually be separate actuation means 165.

In a situation of use, the pump unit without a needle unit mounted thereto is attached to a skin surface of a user where after a needle unit is attached to the pump unit and the needle is inserted. The pump may start automatically when the needle unit is attached thereto or by manual start means (not shown). When it is deemed necessary to exchange the needle unit (e.g. after 1 or 2 days of use), the release means 162 is actuated whereby the needle firstly is retracted to a position within the needle unit and secondly detached from the pump unit. The means for moving the needle from its extended to its retracted position may have any suitable configuration, e.g. the needle may be held in its extended position by biasing means (e.g. a spring) which subsequently is released. Preferably the pump is automatically stopped by this operation just as the needle unit preferably comprises locking means for locking the needle in the retracted position after a single reciprocation of the needle from the initial position to the extended position and back to the retracted position. Alternatively, the coupling and release means 161, 162 may be arranged on the pump unit such that actuation thereof is transferred to the needle unit to retract the needle before the needle unit is released from the pump unit.

As appears from the above, release means in the form of the coupling means has been operated from a first initial state (corresponding to FIG. 25A) through an intermediate state (not shown) to a second state (corresponding to FIG. 25B), whereby operation of the release means from the first to the intermediate state has caused the needle to be moved from an extended position to a retracted position, and operation of the release means from the intermediate to the second state has caused release of the attaching means in the form of the coupling means from the pump unit.

The pump unit shown in FIG. 25A is adapted to be mounted on the skin of a user and used for a given number of days during which the delivery needle can be exchanged any desired number of times, however, the adhesive means may be adapted for removing and remounted the device a number of times, e.g. in case it is deemed necessary to introduce a new needle at a new location. This may be accomplished by using an adhesive material which per se allows the device to be removed and re-mounted a number of times, however, alternatively it may be accomplished by using "renewable" adhesive means.

More specifically, FIG. 25C discloses a drug delivery device 300 of the same general type as shown in FIG. 25A, i.e. a skin-mountable pump unit 301 with a thereto attached needle unit 350, however, the coupling and actuation means are not shown. The lower mounting surface of the pump unit is arranged on a flexible adhesive patch member 370 comprising a lower adhesive surface allowing the pump unit to be mounted on the skin of a user. However, in contrast to the FIG. 25A embodiment, the patch member comprises a "stack" of peelable sheets 371, 372, 373 (e.g. 3 as shown). For illustrative purposes the thickness of the individual sheets and thus the stack is shown somewhat exaggerated. Each of the peelable sheets comprises an upper surface and an adhesive lower surface allowing the peelable sheets to be arranged in a stacked arrangement with their respective upper surfaces attached to the overlying adhesive surface. In the shown embodiment each of the peelable sheets as well as the sheet member directly attached to the pump unit comprises a tab 374, 375, 376 which can be gripped by the user, the tab comprising no adhesive on its lower surface. Advantageously the tabs comprise individual indication means indicating in which order they are to be used (see below). When supplied to the user, the lowermost surface is advantageously covered with a peelable release liner.

In a situation of use the release liner is removed thereby uncovering the adhesive surface of the lowermost peelable sheet (when seen from above as in FIG. 25C), the adhesive surface allowing the delivery device to be attached to the skin of the user. When after a given period of time it is desirable to remove and re-mount the delivery device (which may be either concurrent with, before or after exchange of the needle) the user grips the tab of the lowermost sheet and pulls off the device from the skin surface. After this operation the same tab is used to remove the now used lowermost sheet by simply peeling it off, this operation uncovering a new "fresh" adhesive surface provided on the next sheet in the stack allowing the delivery device to be re-mounted on the skin of the user. This procedure may then be repeated corresponding to the number of peelable sheets, the "last" adhesive surface being provided by the sheet member directly attached to the pump unit. Indeed, the adhesive used and the properties of the upper surface of the individual sheet should be selected to provide safe and reliable attachment of the device to the skin of the user, prevent delaminating of the individual layers during use, yet allowing a used sheet to be peeled off easily.

As appears, the number of times the pump unit can be re-mounted on the skin surface using a fresh adhesive surface is limited to the number of adhesive surfaces provided by the stack, however, if the pump unit (or any other type of skin mountable device such as a sensor device) is intended for a relatively long period of use (either being a prefilled or user fillable unit) it may be desirable to re-mount the unit a further number of times. Addressing this problem, FIG. 25D discloses a drug delivery device 400 of the same general type as shown in FIG. 25C, however, in contrast to the embodiments of FIGS. 25A and 25C the adhesive means is not provided as part of the pump unit but is included as part of an additional base plate unit.

More specifically, the delivery device 400 comprises a base plate unit 490 having a stack of peelable sheets, a pump unit 401 and a needle unit 450. The pump unit and the needle unit are configured to be mounted on the upper surface of the base plate unit by means of mating coupling means 441, 461 on the pump unit respectively the needle unit. Alternatively the needle unit may be attached to the pump unit.

In a situation of use the delivery device of FIG. 25D may be used in the same way as described above with reference to the embodiment of FIG. 25C, but with the difference that the base plate unit can be exchanged a desired number of times.

Although the peelable stacks of FIGS. 25C and 25D are shown in combination with a device of the same type as shown in FIG. 25A, it readily appears that the same stack arrangement with corresponding effect may used in combination with skin-mountable devices of any given nature, e.g. a modular arrangement as in FIG. 25A in which movement of the needle is not functionally coupled to the release of a needle unit from a pump unit, a unitary delivery device comprising an externally arranged needle (e.g. connected to an infusion set) or a sensor device either unitary of modular, just as it may also be used on devices comprising no skin-piercing members, e.g. sensor devices (unitary or modular) based on non-penetrating sensor means.

Figure 26:
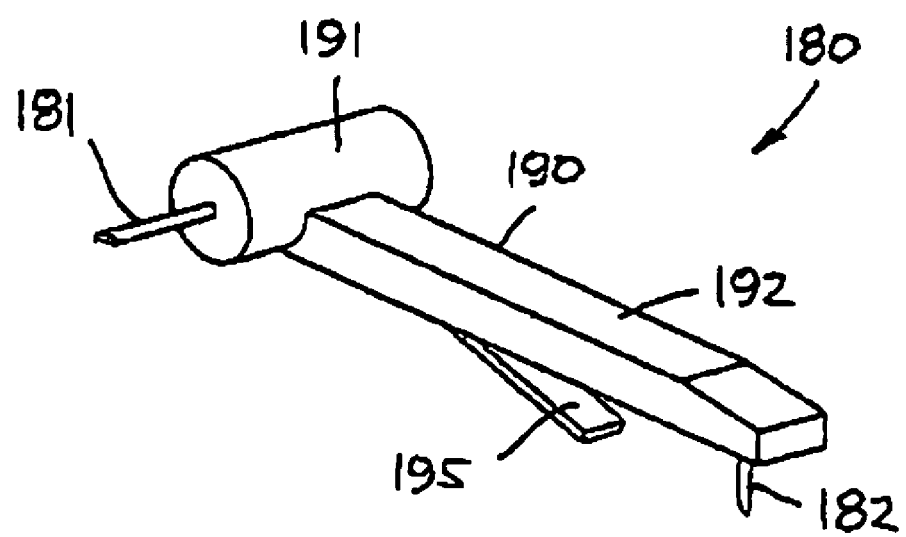
FIG. 26 shows an embodiment of a needle subunit.

FIG. 26 shows a needle subunit 180 suitable for use as part of the needle unit 150 in which it is connected to the needle housing 160 by a hinge allowing the needle subunit to pivot corresponding to a pivoting axis defined by the hinge. More specifically, the needle comprises a needle carrier 190 having a cylindrical hinge portion 191 defining the pivoting axis, and an arm member 192 extending perpendicularly from the hinge portion in respect of the pivoting axis. On a lower surface of the arm member a biasing means is arranged in the form of a leaf spring member 195 adapted to engage a portion of the needle housing. The needle carrier carries a needle having first and second pointed end portions 181, 182 arranged substantially corresponding to the pivoting axis respectively perpendicularly thereto. Correspondingly, the needle housing 160 comprises a first opening allowing the needle penetratable septum to be advanced into fluid communication with the first pointed needle end portion 181, and a second opening in the lower surface allowing the second pointed needle portion end portion 182 to extend therefrom. The openings may be covered by penetratable barrier means whereby the needle housing can be used for providing an enclosure for a sterile needle, e.g. corresponding to FIGS. 23A and 23B. When the needle unit is attached to the pump unit the protruding septum is moved into engagement with the needle, during which operation fluid communication is established between the second needle portion and the reservoir. When the needle is actuated the needle subunit is pivoted from its initial to its second position (with the first needle portion being rotated corresponding to the pivoting axis), the first pointed needle end thereby being moved through the second opening in the needle housing and the aperture in the base plate portion.

In the above described embodiments, the transcutaneous device has been in the form of a unitary needle device (e.g. an infusion needle as shown or a needle sensor (not shown)), however, the transcutaneous device may also be in the form of a cannula or a sensor in combination with an insertion needle which is withdrawn after insertion thereof. For example, the first needle portion may be in the form of a (relatively soft) infusion cannula (e.g. a Teflon® cannula) and a therethrough arranged removable insertion needle. This type of cannula needle arrangement is well known from so-called infusion sets, such infusion sets typically being used to provide an infusion site in combination with (durable) infusion pumps.

Figure 20A:
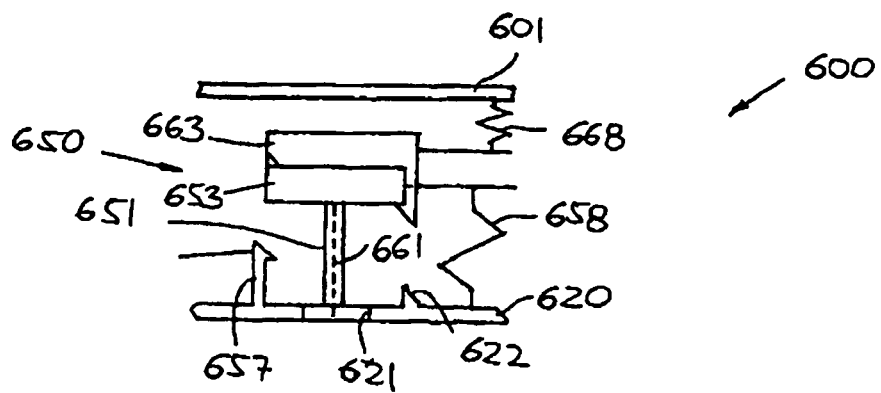
FIGS. 20A and 20B show in a schematic representation a transcutaneous device in the form of a cannula and insertion needle combination.
Figure 20B:
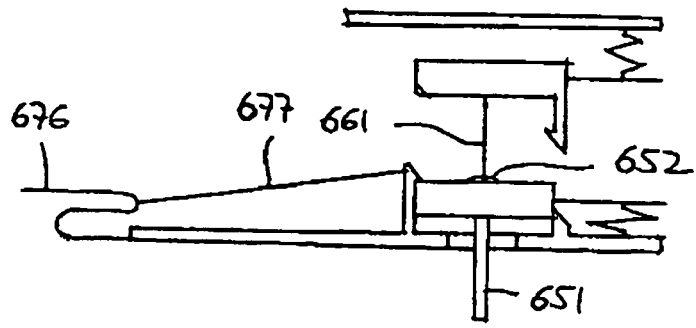

Thus, FIGS. 20A and 20B show in a schematic representation how a cannula and insertion needle combination can be arranged within a housing 601 of in a given medical device 600 (partly shown), e.g. an infusion device or an infusion set. More specifically, the medical device comprises a transcutaneous assembly 650 comprising a combination of a relatively soft cannula 651 (which e.g. may be of the soft "Teflon®" type) carried by a lower member 653 and a pointed insertion needle 661 (e.g. made from medical grade stainless steel) slidably arranged within the cannula and carried by an upper member 663, both members being mounted to allow axial displacement of the cannula respectively the insertion needle. The cannula comprises a proximal inlet (not shown) allowing it to be or to be arranged in fluid communication with a fluid source. The medical device further comprises a base plate 620 with an opening 621 for the cannula as well as a release member 622. The lower member comprises an elastomeric seal 652 through which the insertion needle is arranged. The cannula and the insertion needle may be straight or curved dependent upon how the two members are mounted in the device, e.g. arcuate corresponding to a pivoting axis or straight corresponding to linear movement as illustrated. The upper member comprises a coupling member 667 locking the members together in an initial position with distal end of the insertion needle extending from the distal opening of the cannula as shown in FIG. 20A, and the base plate comprises coupling member 657 for locking the lower member in an extended position with distal end of the cannula extending through the opening in the base plate (see FIG. 20B). Between the housing of the device and the upper member a first spring 668 is arranged biasing the upper member upwards. Correspondingly, the device also comprises a second spring 658 biasing the lower member upwardly. The medical device further comprises a gripping tab 676 and a pulling member 677 corresponding to the embodiment shown in FIG. 1.

In a situation of use the assembly is moved downwardly, either manually or by a releasable insertion aid, e.g. a spring loaded member acting through an opening in the housing (not shown) whereby the cannula with the projecting insertion needle is inserted through the skin of a subject. In this position the lower member engages the coupling member 657 to thereby lock the cannula in its extended position, just as the coupling member 667 is released by the release member 622 thereby allowing the upper member to return to its initial position by means of the first spring.

When the user intends to remove the delivery device from the skin surface, the user grips the gripping portion of the tab and pulls it in a first direction substantially in parallel with the skin surface, by which action the flexible strip 677 releases the coupling member 657 from the lower member whereby the lower member and thereby the cannula is retracted by means of the second spring. When the cannula has been withdrawn from the skin, the user uses the now unfolded tab to pull off the entire delivery device from the skin surface, for example by pulling the tab in a direction away from the skin surface.

In the above-described embodiments a reservoir unit or a drug delivery device comprising a reservoir has been described, however, for better illustrating the principles of the present invention, the means for expelling a drug from the reservoir has been omitted in some of the figures. Such expelling means, which as the reservoir does not form part of the present invention in its basic form, may be of any type which would be suitable for arrangement within a skin-mountable drug delivery device or reservoir unit. Further, as the needle of the present invention also may be in the form of a needle sensor, the interior of the corresponding medical device may comprise sensor means adapted to cooperate with the needle sensor.

Figure 27A:
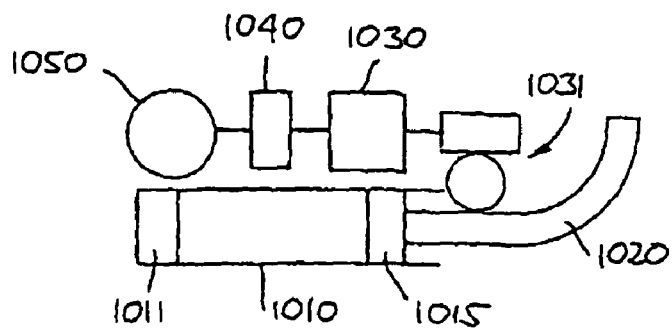
FIGS. 27A-27E show different expelling means suitable for use with drug delivery devices.

In FIGS. 27A-27E examples of expelling means suitable for use with the present invention are shown schematically, however, these are merely examples, just as the shown arrangement of the individual components not necessarily are suitable for direct application in the above shown delivery devices. More specifically, FIG. 27A shows a pump arrangement comprising a drug-containing cartridge 1010 forming a reservoir and having a distal closure member 1011 allowing a needle to be connected, and a piston 1015 slidingly arranged there within, a flexible toothed piston rod 1020 (for example as disclosed in U.S. Pat. No. 6,302,869), an electric motor 1030 which via a worm-gear arrangement 1031 drives the piston rod to expel drug from the cartridge, the motor being controlled by control means 1040 and the energy for the control means and the motor being provided by a battery 1050. The pump may be activated when the needle is inserted (by means not shown) or by separate user-actuatable means (not shown) after the inserter has been detached form the delivery device.

Figure 27B:
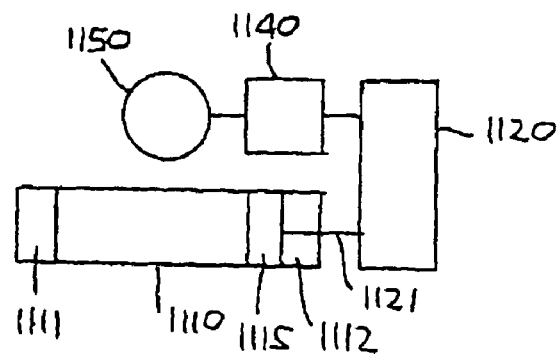

FIG. 27B shows a pump arrangement comprising a drug-containing cartridge 1110 having distal and proximal closure members 1111, 1112, and a piston 1115 slidingly arranged there within, gas generating means 1120 in fluid communication with the interior of the cartridge via conduit 1121 for driving the piston to expel drug from the cartridge, the gas generating means being controlled by control means 1140 and the energy for the control means and the gas generation being provided by a battery 1150. The pump may be activated as indicated above. A detailed disclosure of such gas generating means for a drug delivery device can be found in e.g. U.S. Pat. No. 5,858,001.

Figure 27C:
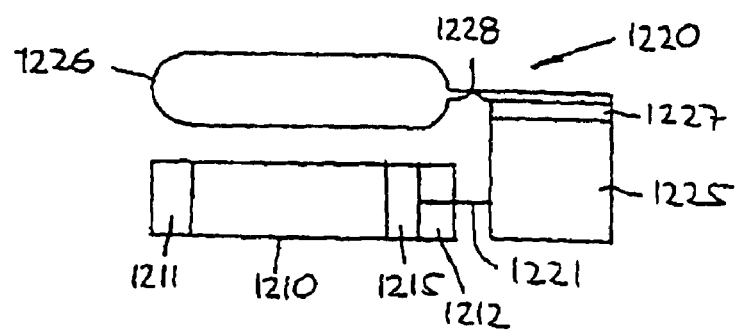

FIG. 27C shows a pump arrangement comprising a drug-containing cartridge 1210 having distal and proximal closure members 1211, 1212, and a piston slidingly 1215 arranged there within, an osmotic engine 1220 in fluid communication with the interior of the cartridge via conduit 1221 for driving the piston to expel drug from the cartridge. The osmotic engine comprises a first rigid reservoir 1225 containing a salt-solution and a second collapsible reservoir 1226 containing water, the two reservoirs being separated by a semi-permeable membrane 1227. When supplied to the user, the fluid connection 1228 between the second reservoir and the membrane is closed by a user-severable membrane (e.g. a weak weld) which, when severed, will allow the osmotic process to start as water is drawn from the second reservoir through the membrane and into the first reservoir. The pump may be activated as indicated above. A detailed disclosure of the osmotic drive principle can be found in e.g. U.S. Pat. No. 5,169,390.

Figure 27D:
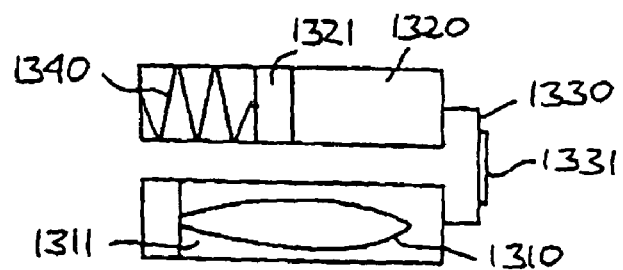

FIG. 27D shows a pump arrangement comprising a drug-containing flexible reservoir 1310 arranged within a rigid fluid-filled secondary reservoir 1311 in fluid communication with a primary reservoir 1320 through a conduit 1330 comprising a flow restrictor 1331. The primary reservoir is in the form of a cartridge with a moveable piston 1321 and contains a viscous drive fluid. A spring 1340 is arranged to act on the piston to drive fluid from the first to the second reservoir thereby expelling drug from the flexible reservoir when the latter is connected to an infusion needle (not shown). The flow rate will be determined by the pressure generated by the spring in the drive fluid, the viscosity of the drive fluid and the flow resistance in the flow restrictor (i.e. bleeding hole principle). The pump may be activated by straining the spring or by releasing a pre-stressed spring, either when the needle is inserted (by means not shown) or by separate user-actuatable means (not shown) after the inserter has been detached form the delivery device. An example of this principle used for drug infusion is known from DE 25 52 446. In an alternative configuration, the drug reservoir may be pressurized directly to expel the drug via a flow restrictor, e.g. as disclosed in U.S. Pat. No. 6,074,369.

Figure 27E:
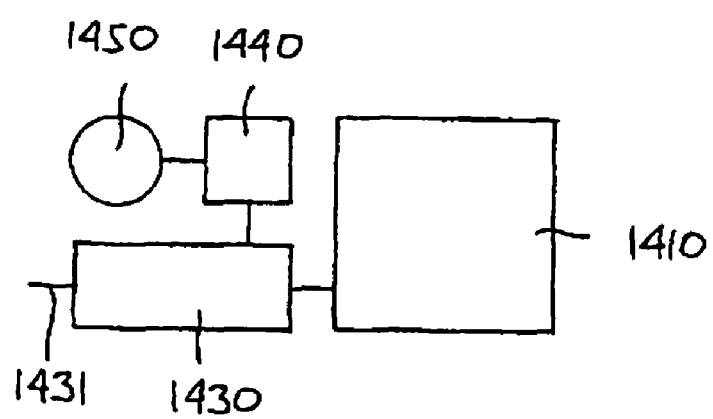

FIG. 27E shows a pump arrangement comprising a membrane pump 1430 having an outlet 1431 and control means 1440 for controlling the pump, the energy for the control means and the pump being provided by a battery 1450. The membrane pump is (in a situation of use) connected to a reservoir 1410 from which drug is sucked through the pump and expelled through the outlet. The reservoir may be provided with venting means or it may be in the form of a flexible, collapsible reservoir whereby venting means can be dispensed with. The pump may be activated when the needle is inserted (by means not shown) or by separate user-actuatable means (not shown) after the inserter has been detached form the delivery device.

In the above description of the preferred embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A medical device, comprising:
a lower mounting surface adapted for application towards the skin of a subject,
a sheet member extending peripherally relative to the mounting surface and having a lower adhesive surface for securing the mounting surface relative to the skin,
a transcutaneous device adapted to penetrate the skin of the subject and being mounted for movement between an extended position in which the transcutaneous device projects relative to the lower mounting surface and a retracted position in which the transcutaneous device is retracted relative to the lower mounting surface,
a release attached directly to a peripheral portion of the sheet member, the release comprising a user gripable portion moveable relative to the lower mounting surface, the user gripable portion being operatable from a first condition through an intermediate condition to a second condition,
whereby operation of the user gripable portion from the first to the intermediate condition causes the transcutaneous device to be moved from the extended position to the retracted position, and operation of the user gripable portion from the intermediate to the second condition causes release of the sheet member from the skin.

2. A medical device as in claim 1, wherein the release comprises:
transcutaneous device retraction means operatable between a first state in which the transcutaneous device projects relative to the lower surface and a second state in which the transcutaneous device is retracted relative to the lower surface, the transcutaneous device retraction means being moved between its first and second states when the user gripable portion is operated from the first to the intermediate state.

3. A medical device as in claim 2, wherein:
the transcutaneous device retraction means is operatable connected to the user gripable portion such that the transcutaneous device retraction means is moved between its first and second states when the user gripable portion is operated from the first to the intermediate state, and wherein
the medical device is pulled off the skin of the subject when the user gripable portion is operated from its intermediate state to its second state.

4. A medical device as in claim 2, wherein the user gripable portion and the transcutaneous device retraction means are operatable connected to each other allowing movement of the user gripable portion to be transferred to the transcutaneous device retraction means.

5. A medical device as defined in claim 2, wherein the transcutaneous device retraction means comprises a flexible strip portion arranged below a portion of the transcutaneous device, whereby the flexible strip portion will lift the transcutaneous device from the extended position to the retracted position when the user gripable portion is operated from the first to the intermediate state.

6. A medical device as in claim 1, wherein the transcutaneous device is mounted for movement between an initial position in which the transcutaneous device is retracted relative to the lower surface and the extended position in which the transcutaneous device projects relative to the lower surface.

7. A medical device as in claim 1, wherein the transcutaneous device is a fluid delivery device comprising a distal end adapted to penetrate the skin of the subject and a proximal end adapted to be arranged in fluid communication with a fluid supply.

8. A medical device as in claim 1, further comprising coupling means for releasable securing the transcutaneous device unit to a mating structure, wherein the transcutaneous device is a fluid delivery device comprising a distal end adapted to penetrate the skin of the subject and a proximal end adapted to be arranged in fluid communication with a fluid supply.

9. A medical device as in claim 1, wherein the transcutaneous device is a fluid delivery device, the medical device further comprising:
a housing,
a reservoir adapted to contain a liquid drug and comprising an outlet means allowing the fluid delivery device to be arranged in fluid communication with an interior of the reservoir, and
expelling means for, in a situation of use, expelling a drug out of the reservoir and through the skin of the subject via the fluid delivery device.

10. A medical device as in claim 1, in combination with a pump unit comprising: —a mounting surface adapted for application against the skin of a subject,
a reservoir adapted to contain a liquid drug, expelling means for, in a situation of use, expelling a drug out of the reservoir and through the skin of the subject via the transcutaneous device, wherein the attaching means is adapted for securing the medical device to the pump unit and thereby relative to the skin of the subject, and whereby operation of the release means from the first to the intermediate state causes the transcutaneous device to be moved from the extended position to the retracted position, and operation of the release means from the intermediate to the second state causes release of medical device from the pump unit.

11. A combination as in claim 10, wherein a receiving portion of the pump unit and a corresponding portion of the medical device comprise the attaching means in the form of mating, releasable coupling means allowing the medical unit to be secured to the pump unit.

12. A combination as in claim 10, wherein the mounting surface comprises an aperture, the transcutaneous device unit being secured relative to the mounting surface with the transcutaneous device in register with the aperture, the transcutaneous device being adapted to extend through the aperture in its extended position.

13. A combination as in claim 10, wherein the transcutaneous device is moved from its initial to its extended position when the medical device and the pump unit are attached to each other.

14. A medical device as in claim 1, in combination with a pump unit comprising: —a reservoir adapted to contain a liquid drug, expelling means for, in a situation of use, expelling a drug out of the reservoir and through the skin of the subject via the transcutaneous device, wherein the medical device and the pump unit comprise mating coupling means allowing the pump unit to be releasable attached to the medical device.

15. A medical device as in claim 1, in combination with a pump unit and a base plate unit, the base plate unit comprising:

an upper surface and a lower mounting surface adapted for application against the skin of a subject, the mounting surface comprising mounting means having an adhesive surface, the pump unit comprising:

a reservoir adapted to contain a liquid drug and comprising an outlet means allowing the transcutaneous device to be arranged in fluid communication with an interior of the reservoir, expelling means for, in a situation of use, expelling a drug out of the reservoir and through the skin of the subject via the transcutaneous device, the pump unit and the base plate unit comprising mating, releasable coupling means allowing the pump unit to be secured to the base plate unit, wherein the attaching means is adapted for securing the medical device to the pump unit and/or the base plate unit and thereby relative to the skin of the subject, and whereby operation of the release means from the first to the intermediate state causes the transcutaneous device to be moved from the extended position to the retracted position, and operation of the release means from the intermediate to the second state causes release of medical device from the pump unit.

16. A medical device as in claim 1, further comprising a first peelable sheet having an upper surface and an adhesive lower surface, the upper surface being adapted for peelable detachment from a lower mounting surface.

17. A medical device or combination as in claim 16, comprising at least one further peelable sheet, each further peelable sheet comprising an upper surface and an adhesive lower surface, the first and the further peelable sheets being arranged in a stacked arrangement with their respective upper surfaces attached to the overlying adhesive surface.

18. A medical device as in claim 1, wherein the portion of the transcutaneous device adapted to penetrate the skin of the subject is in the form of a hollow metallic needle comprising an outer smooth coating of a polymeric material.

19. A medical device comprising:

a mounting surface adapted for application to a skin site, a sheet member extending peripherally relative to the mounting surface and having a lower adhesive surface for securing the mounting surface relative to the skin an adhesive for securing the mounting surface to the skin site, —a transcutaneous device adapted to penetrate the skin at the skin site, the transcutaneous device being mounted for movement between an initial position in which the transcutaneous device is retracted relative to the lower surface and an extended position in which the transcutaneous device projects relative to the lower surface, and for movement between the extended position and a retracted position in which the transcutaneous device is retracted relative to the lower surface, actuation means comprising a first user gripable portion moveable relative to the mounting surface, the first user gripable portion being moveable to cause the transcutaneous device to be moved from the initial position to the extended position, and a release attached directly to a peripheral portion of the medical device and comprising a second user gripable portion moveable relative to the housing, the second user gripable portion being moveable to cause the transcutaneous device to be moved from the extended position to the retracted position, the release further allowing a pulling force to be applied to the peripheral portion of the medical device to thereby remove the medical device when secured to the skin site, wherein the release is attached to a peripheral portion of the sheet member, wherein in an initial state the first user gripable portion at least partially covers the second user gripable portion, such that the second user gripable portion is exposed when the first user gripable portion is moved to cause the transcutaneous device to be moved from the initial position to the extended position.

20. A medical device comprising:

a mounting surface adapted for application towards a skin site, a sheet member extending peripherally relative to the mounting surface and having a lower adhesive surface for securing the mounting surface relative to the skin a transcutaneous device adapted to penetrate the skin at the skin site, the transcutaneous device being mounted for movement between an initial position in which the transcutaneous device is retracted relative to the lower surface and an extended position in which the transcutaneous device projects relative to the lower surface, and for movement between the extended position and a retracted position in which the transcutaneous device is retracted relative to the lower surface, actuation means comprising a first user actuatable portion being actuatable to cause the transcutaneous device to be moved from the initial position to the extended position, and release means comprising a second user actuatable portion actuatable to cause the transcutaneous device to be moved from the extended position to the retracted position, wherein the release means cannot be actuated before the actuation means has been actuated and wherein the release means is attached directly to a peripheral portion of the sheet member.

21. A medical device as in claim 19, wherein the transcutaneous device is a fluid delivery device, the medical device further comprising:

a reservoir adapted to contain a liquid drug and comprising an outlet means allowing the fluid delivery device to be arranged in fluid communication with an interior of the reservoir, and expelling means for, in a situation of use, expelling a drug out of the reservoir and through the skin of the subject via the fluid delivery device.

22. A medical device comprising:

a mounting surface for mounting the device towards the skin of a user;

a sheet member extending peripherally relative to the mounting surface and having a lower adhesive surface for securing the mounting surface relative to the skin a transcutaneous device for penetrating the skin of the user, the transcutaneous device being moveable between an extended position and a retracted position;

a release comprising a user graspable potion, the user graspable portion being moveable to cause the transcutaneous device to be moved from the extended position to the retracted position, the release further being coupled to the medical device in a manner that allows the user to exert a force on the medical device to remove the medical device away from the user's skin after the transcutaneous device has been moved from the extended position to the retracted position, wherein the release is attached directly to a peripheral portion of the sheet member.

23. The device of claim 22, further comprising an adhesive on the mounting surface.

24. An apparatus comprising:

a surface, a sheet member extending peripherally relative to the surface and having a lower adhesive surface for securing the surface relative to the skin a transcutaneous device adapted to penetrate the skin of a subject, the transcutaneous device being moveable between an extended position in which the needle projects relative to the surface and a retracted position in which the needle is retracted relative to the surface, a coupling for releasably securing the transcutaneous device unit to a mating structure, a release operatable from a first state through an intermediate state to a second state, wherein operation of the release from the first to the intermediate state causes the transcutaneous device to be moved from the extended position to the retracted position, and operation of the release from the intermediate to the second state causes release of the coupling and wherein the release is attached directly to a peripheral portion of the sheet member.

* * * * *